United States Patent [19]

Howson et al.

[11] Patent Number: 4,908,017
[45] Date of Patent: Mar. 13, 1990

[54] FAILSAFE APPARATUS AND METHOD FOR EFFECTING SYRINGE DRIVE

[75] Inventors: David C. Howson, Denver; Michael W. Fellinger, Boulder; John A. Popken, Longmont; Richard M. Altobellis, Lyons; Bennett J. Scharf, Boulder; Walter E. Oshetski, Longmont, all of Colo.

[73] Assignee: Ivion Corporation, Englewood, Colo.

[21] Appl. No.: 80,566

[22] Filed: Jul. 31, 1987

Related U.S. Application Data

[63] Continuation-in-part of Ser. No. 734,028, May 14, 1985, abandoned.

[51] Int. Cl.⁴ .............................................. A61M 5/14
[52] U.S. Cl. ..................... 604/67; 604/154; 128/DIG. 1; 128/DIG. 12
[58] Field of Search ............ 604/31, 65, 67, 151, 604/154, 155, 246; 128/DIG. 1, DIG. 12, DIG. 13

[56] References Cited

U.S. PATENT DOCUMENTS

| | | | |
|---|---|---|---|
| 2,764,980 | 10/1956 | Smith | 128/DIG. 1 |
| 3,395,704 | 8/1968 | Frey et al. | 128/DIG. 1 |
| 4,137,913 | 2/1979 | Georgi | 604/67 |
| 4,255,096 | 3/1981 | Coker, Jr. et al. | 128/DIG. 1 |
| 4,342,311 | 8/1982 | Whitney et al. | |
| 4,417,889 | 11/1983 | Choi | |
| 4,435,173 | 3/1984 | Siposs et al. | 128/DIG. 1 |
| 4,529,401 | 7/1985 | Leslie et al. | 128/DIG. 1 |
| 4,563,175 | 1/1986 | LaFond | 128/DIG. 12 |
| 4,627,835 | 12/1986 | Fenton, Jr. | 604/154 |
| 4,652,260 | 3/1987 | Fenton, Jr. et al. | 604/154 |
| 4,676,776 | 6/1987 | Howson | 604/31 |
| 4,828,545 | 5/1989 | Epstein et al. | 604/67 |
| 4,838,856 | 6/1989 | Mulreany | 604/65 |

FOREIGN PATENT DOCUMENTS 0092712 11/1983 European Pat. Off. ............. 604/131

OTHER PUBLICATIONS

NASA Technical Briefs, vol. 8, No. 4, MFS-25119, Summer 1984.
"Microcomputers in Safety Technique" by H. Holscher and J. Rader (Germany 1986).

Primary Examiner—Stephen C. Pellegrino
Assistant Examiner—Ralph Lewis
Attorney, Agent, or Firm—Beaton & Swanson

[57] ABSTRACT

Failsafe apparatus and method are disclosed for controlling fluid flow from syringes. One or more syringes are positioned so that the piston of each syringe is caused to be precisely displaced to thereby safely deliver medicament from the syringe to a patient. To effect movement of each piston, a rack is provided, either as a part of the piston or secured thereto, and longitudinal movement of each rack is effected by rotating an associated pinion gear that is connected with a pulse-driven, stepper motor utilized in a power-efficient electromechanical configuration, with the operation of the stepper motor being accomplished through dual-redundant state machines controlled by a pre-programmed memory unit, and with the apparatus being repeatedly subjected to a plurality of error checks and data integrity verifications to assure continued proper operation.

18 Claims, 19 Drawing Sheets

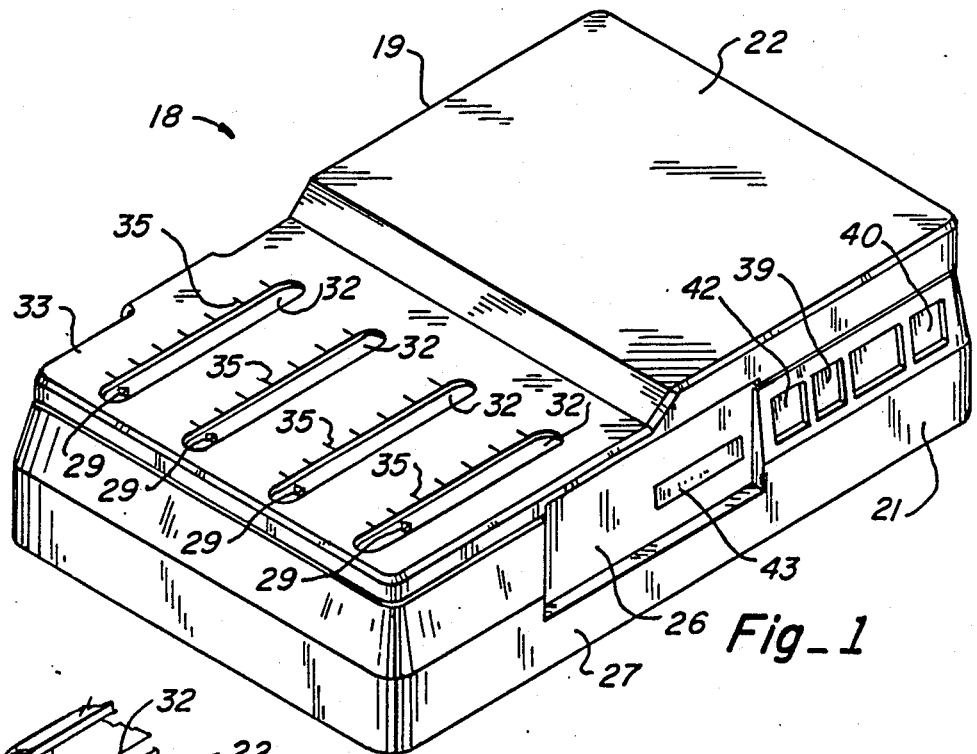
Fig_1
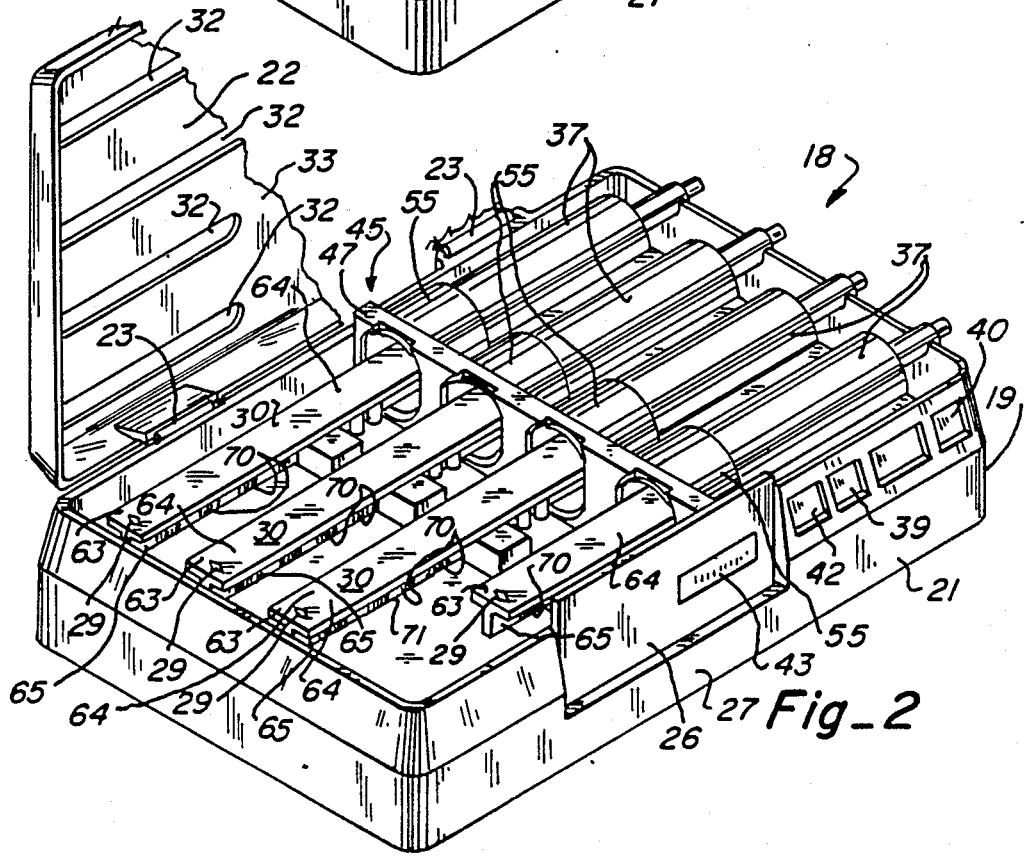
Fig_2

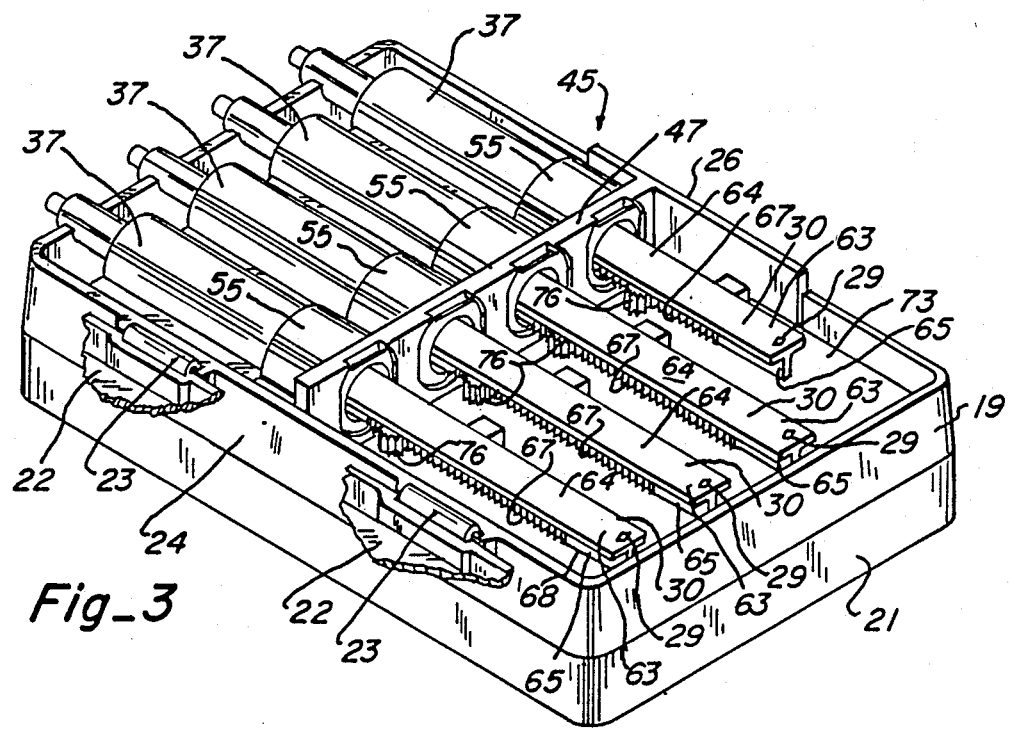
Fig_3
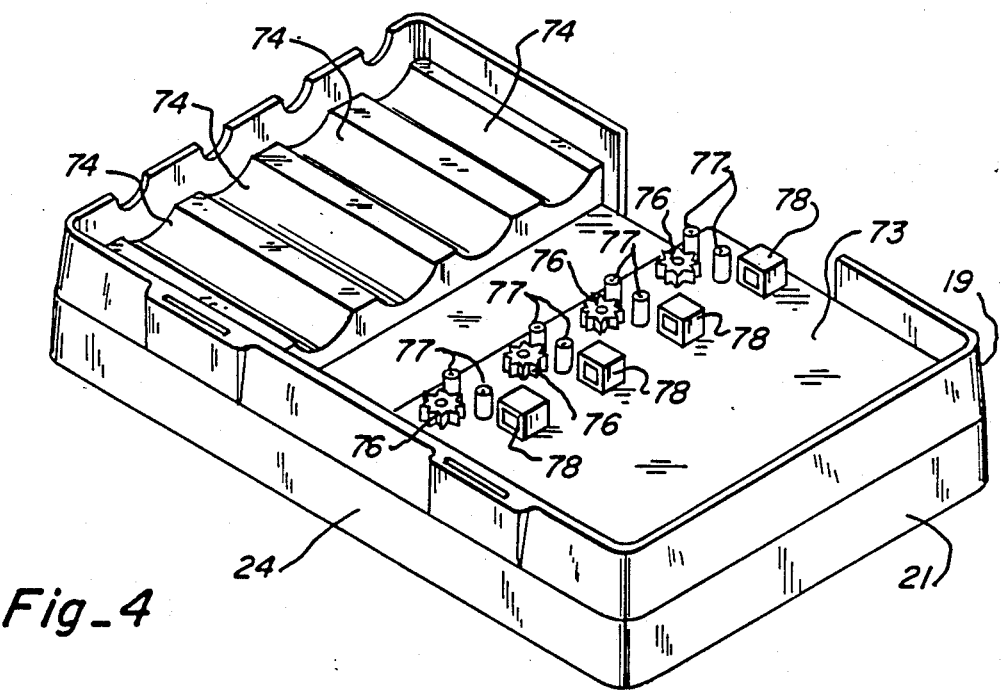
Fig_4

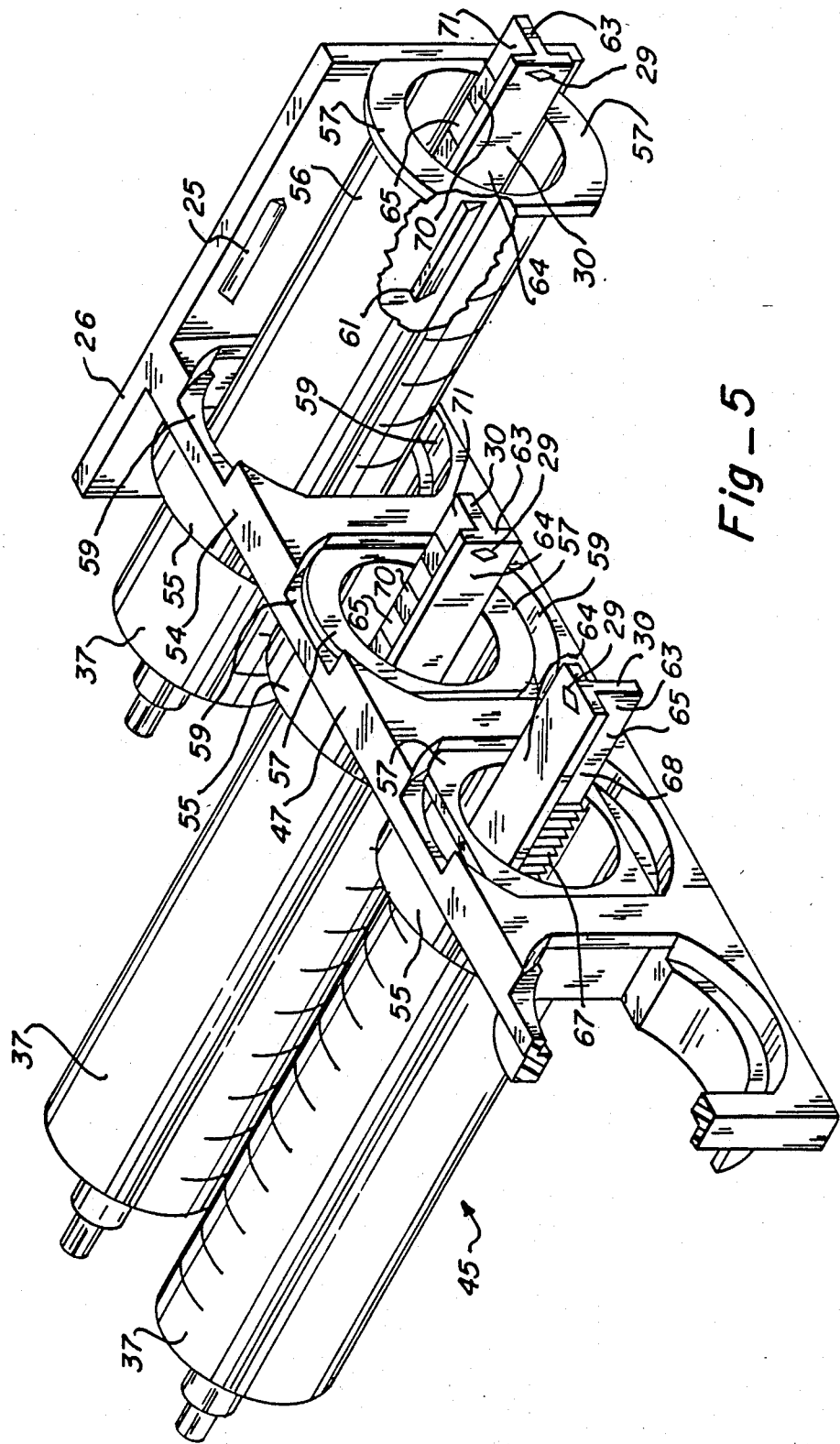

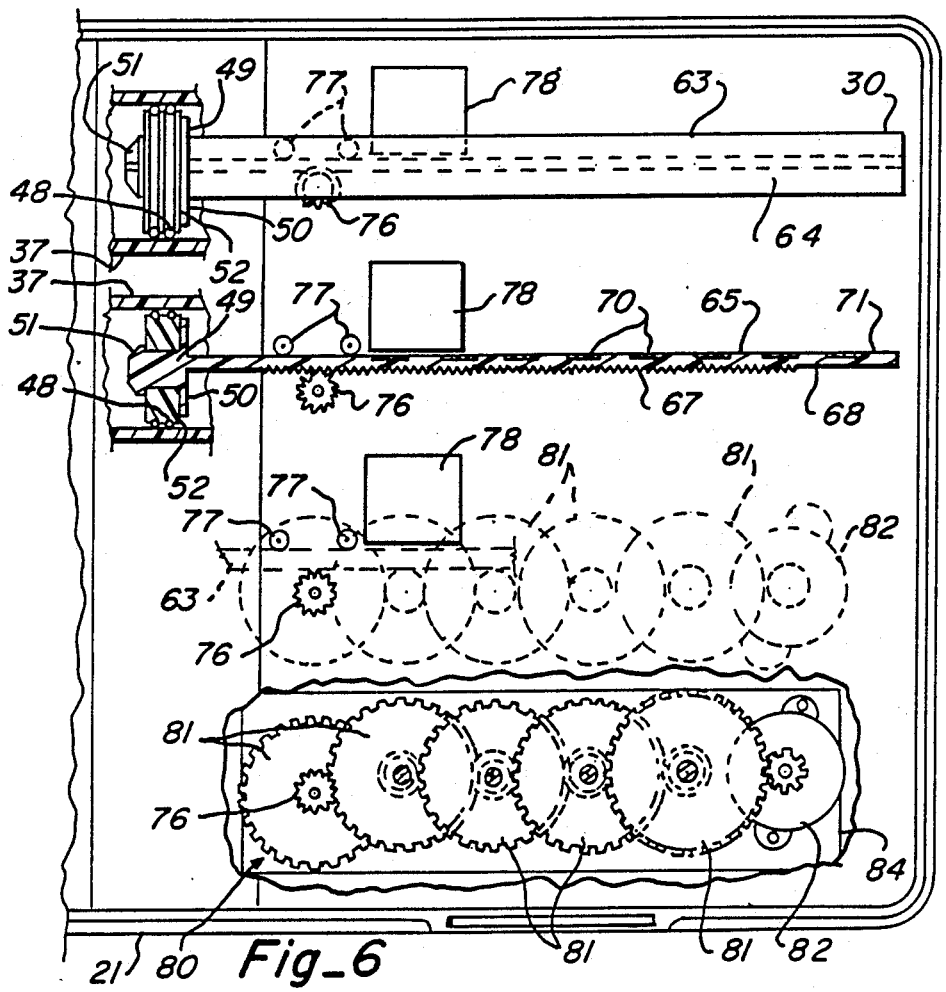
Fig_6
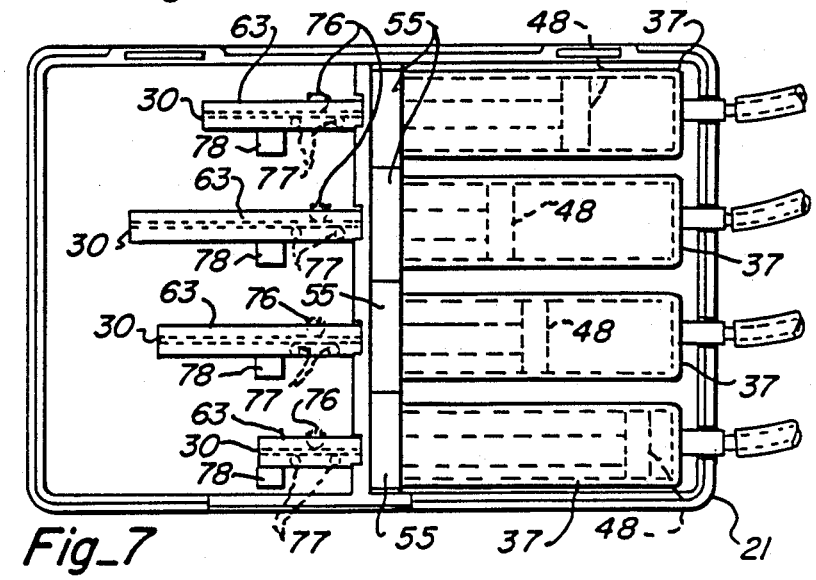
Fig_7

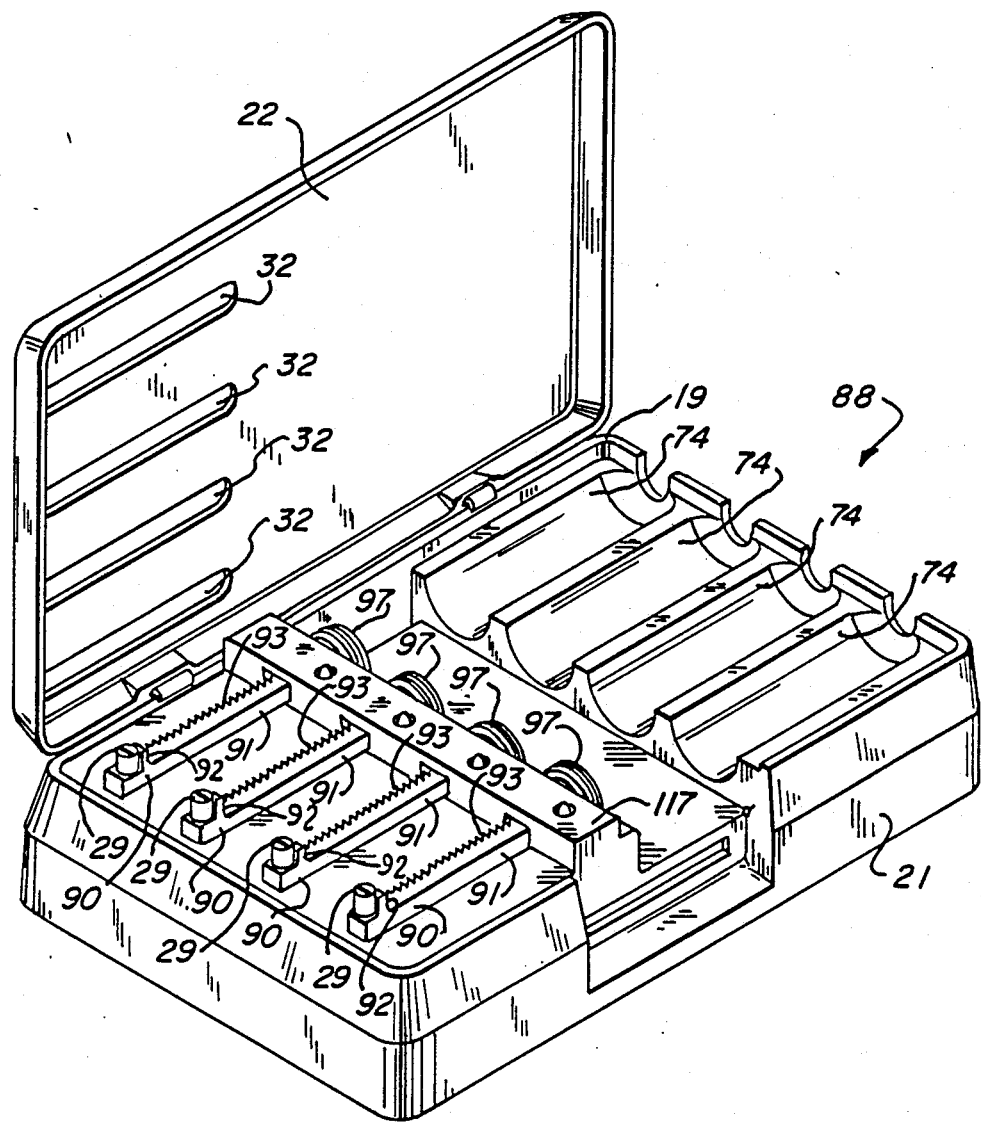
Fig_8

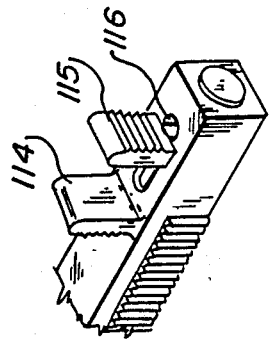
Fig_10A
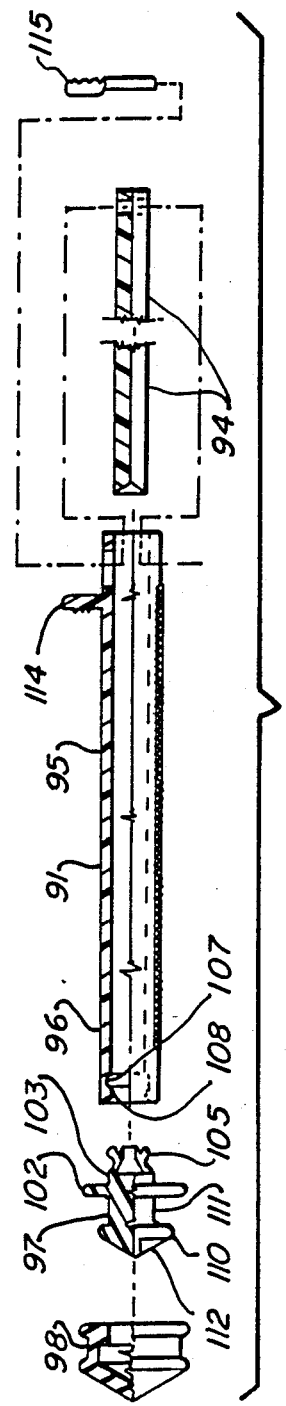
Fig_9
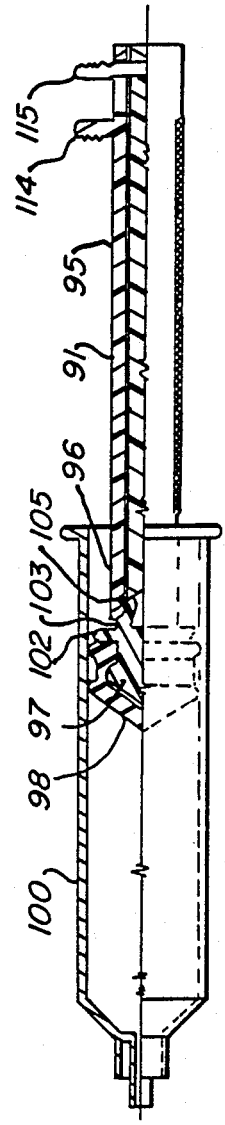
Fig_10
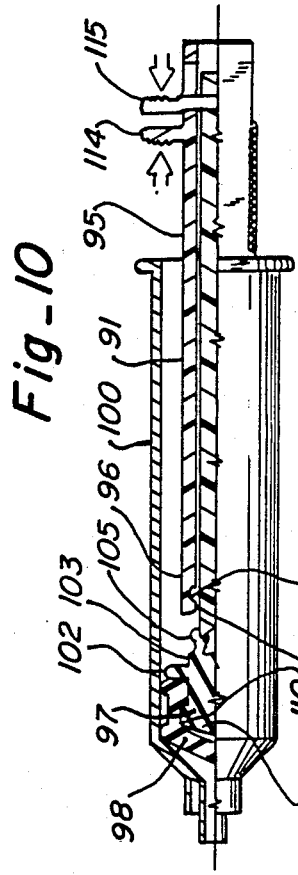
Fig_11

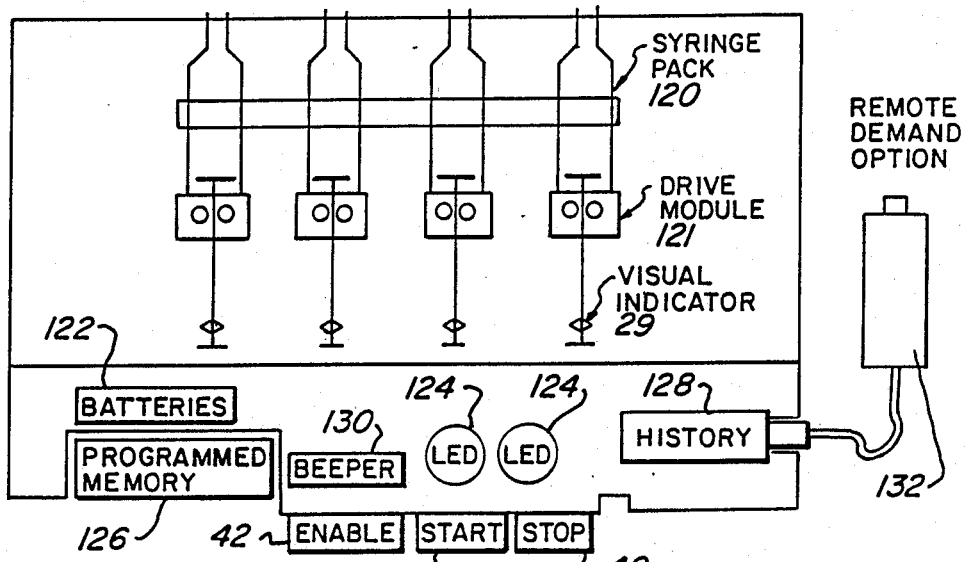
Fig_12
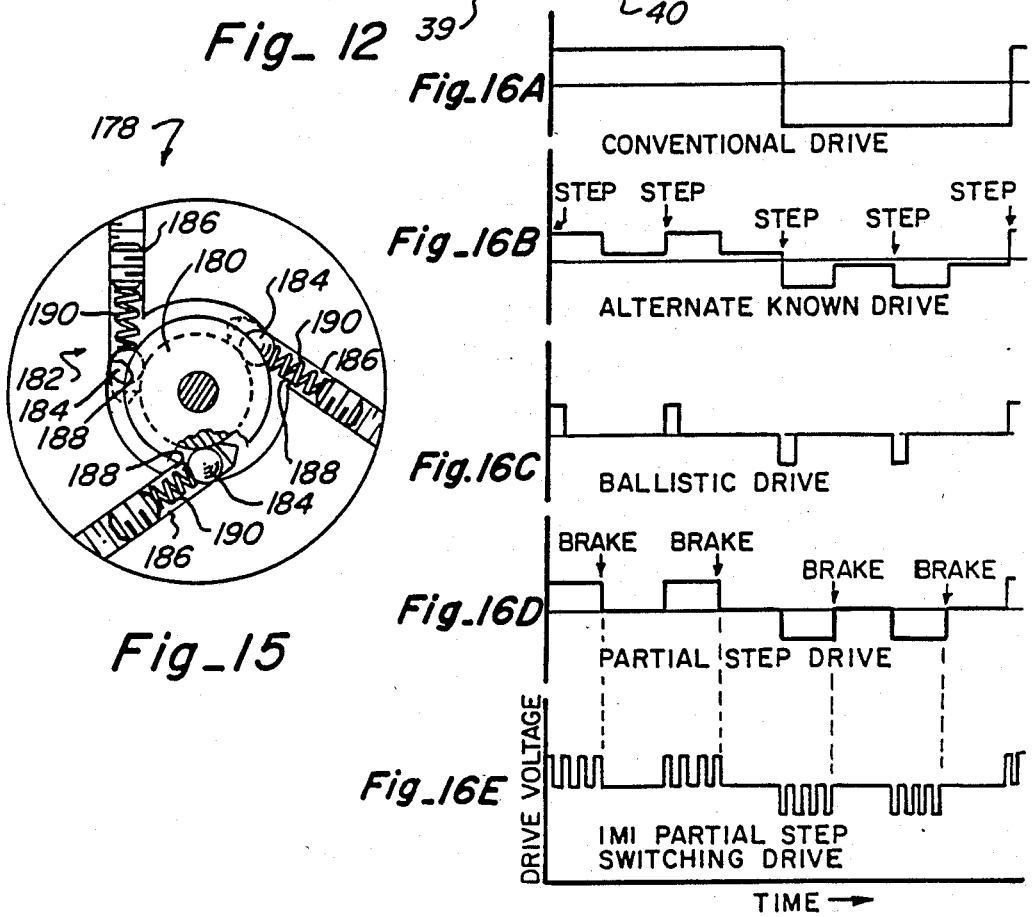
Fig_15
Fig.16A CONVENTIONAL DRIVE
Fig.16B ALTERNATE KNOWN DRIVE
Fig.16C BALLISTIC DRIVE
Fig.16D PARTIAL STEP DRIVE
Fig.16E IMI PARTIAL STEP SWITCHING DRIVE

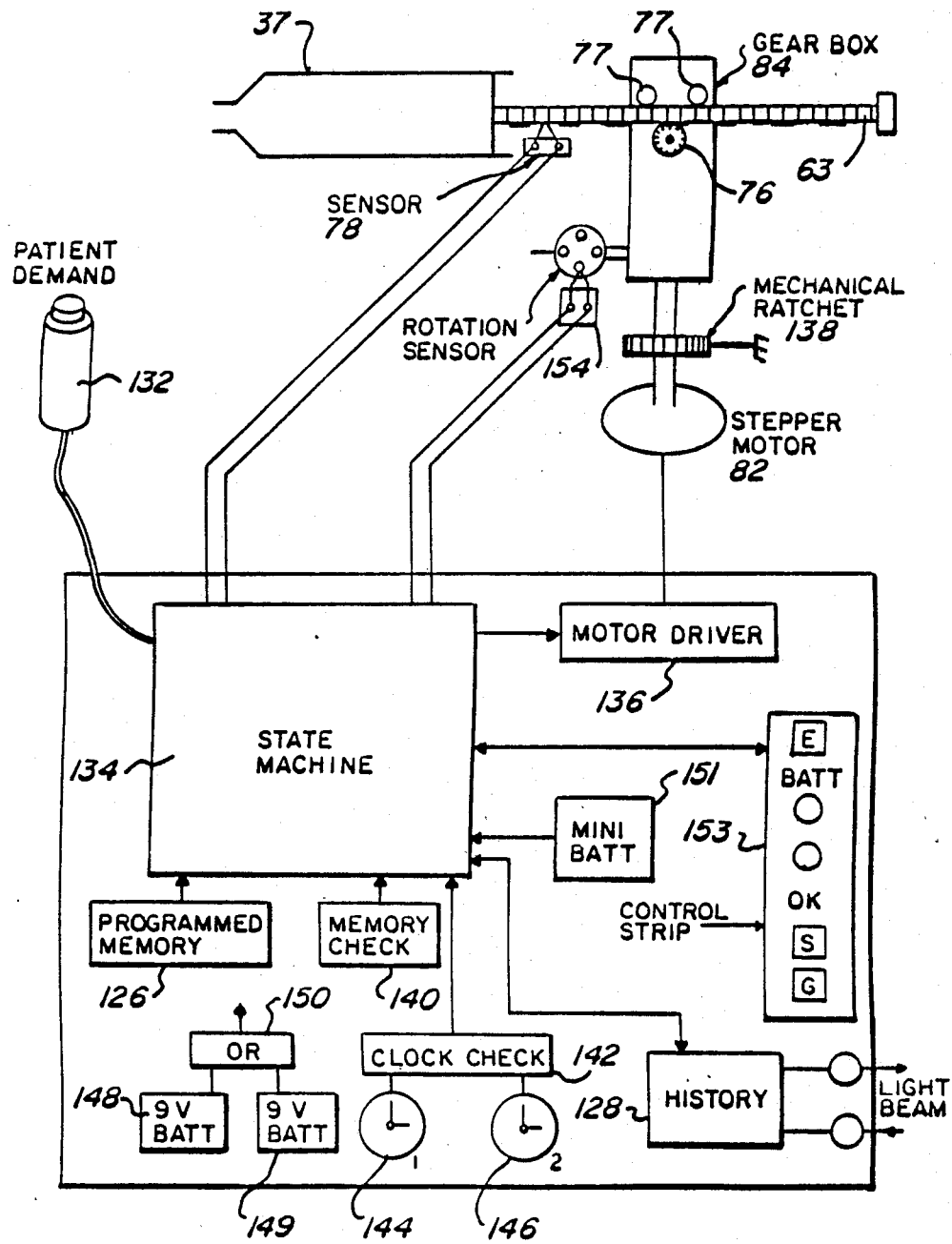
Fig_13

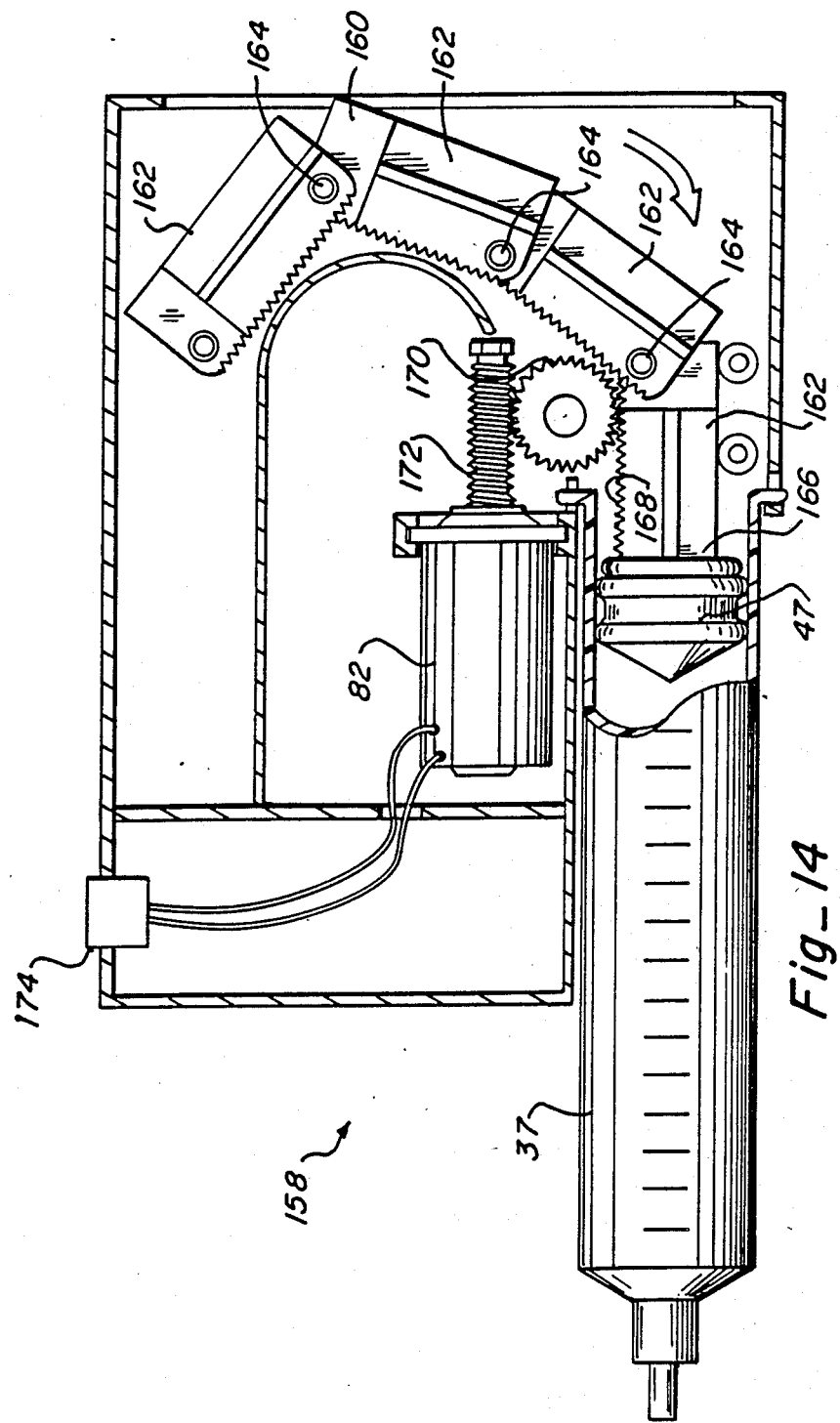
Fig_14

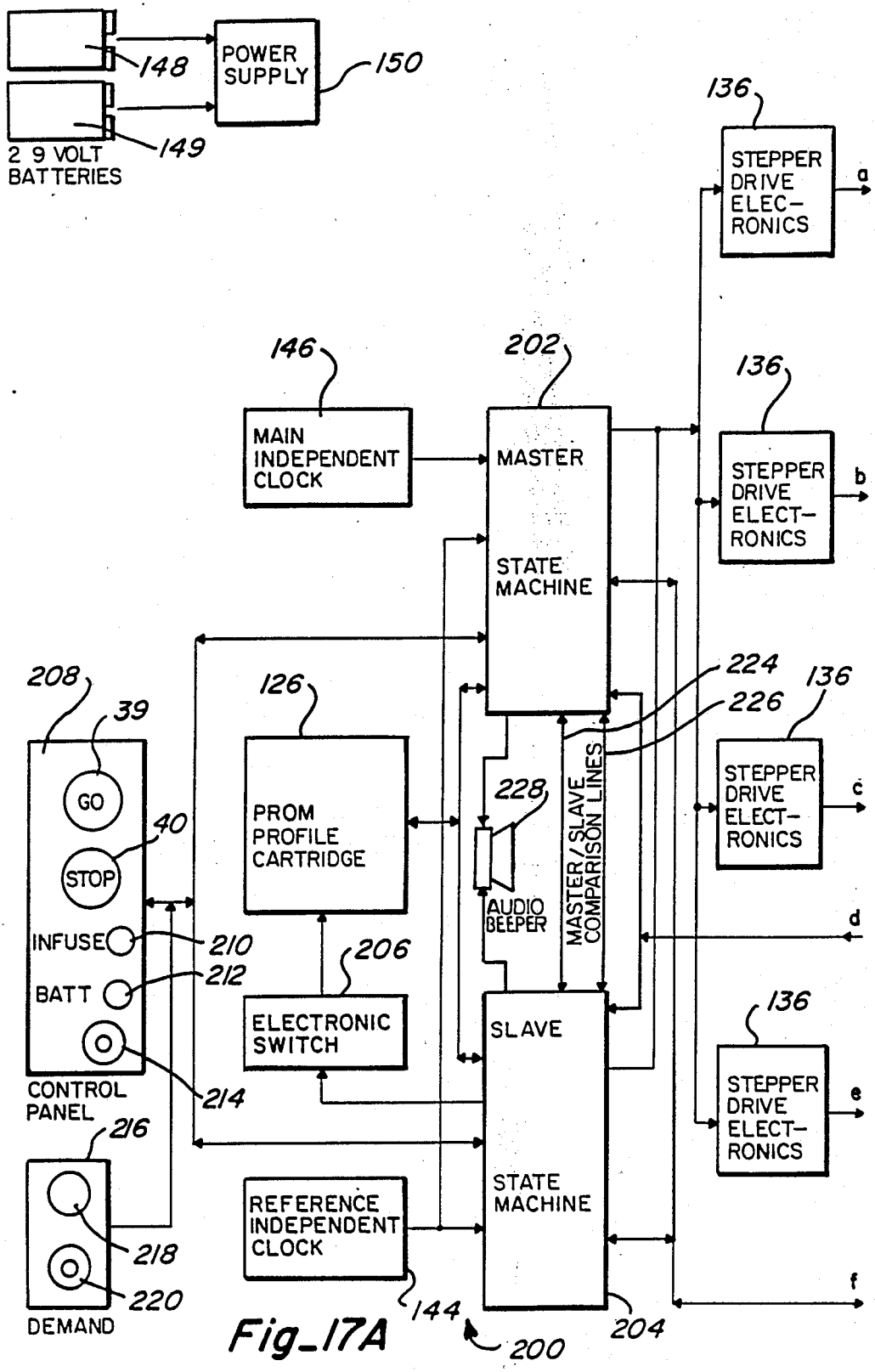
Fig_17A

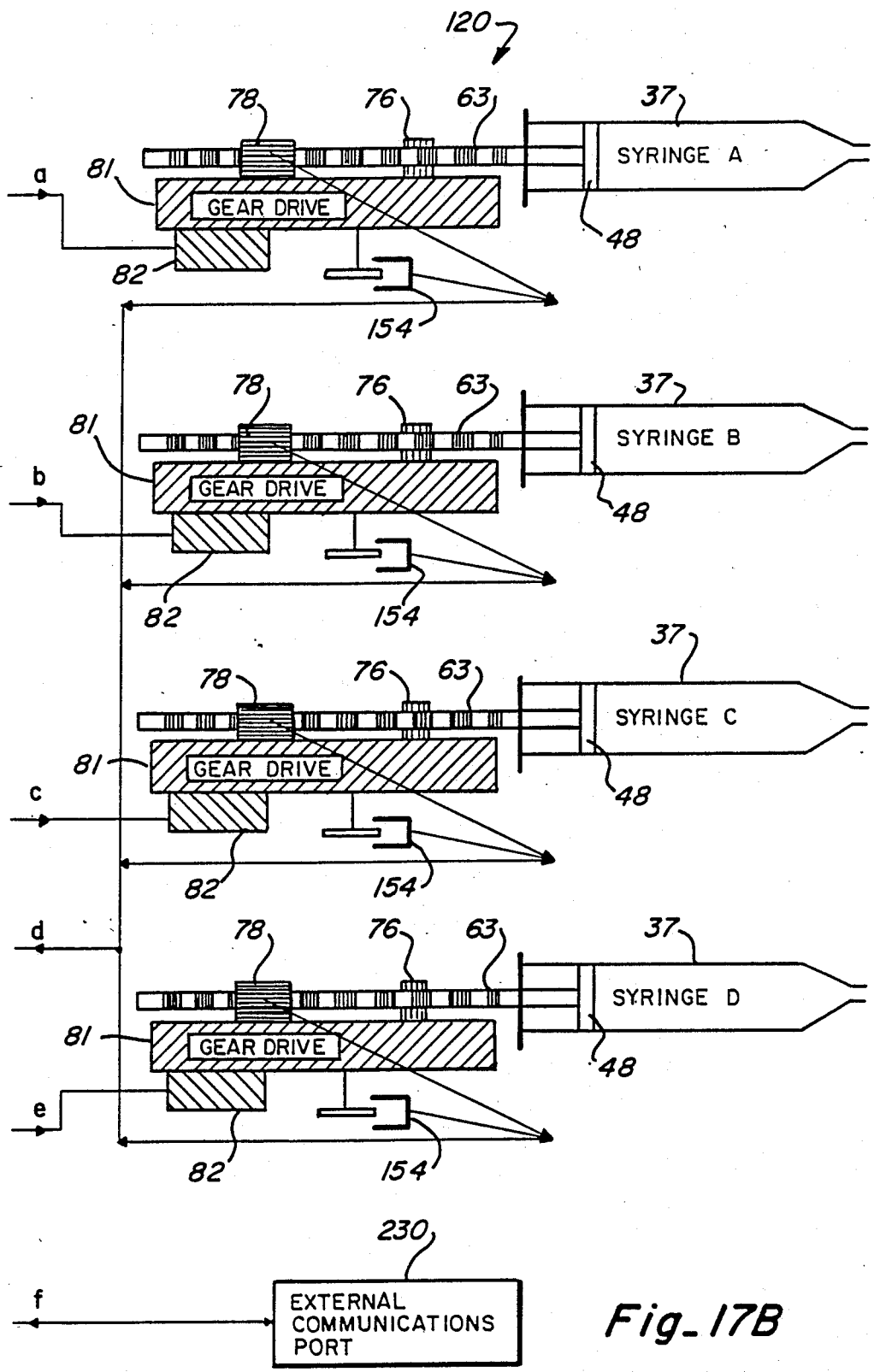
Fig_17B

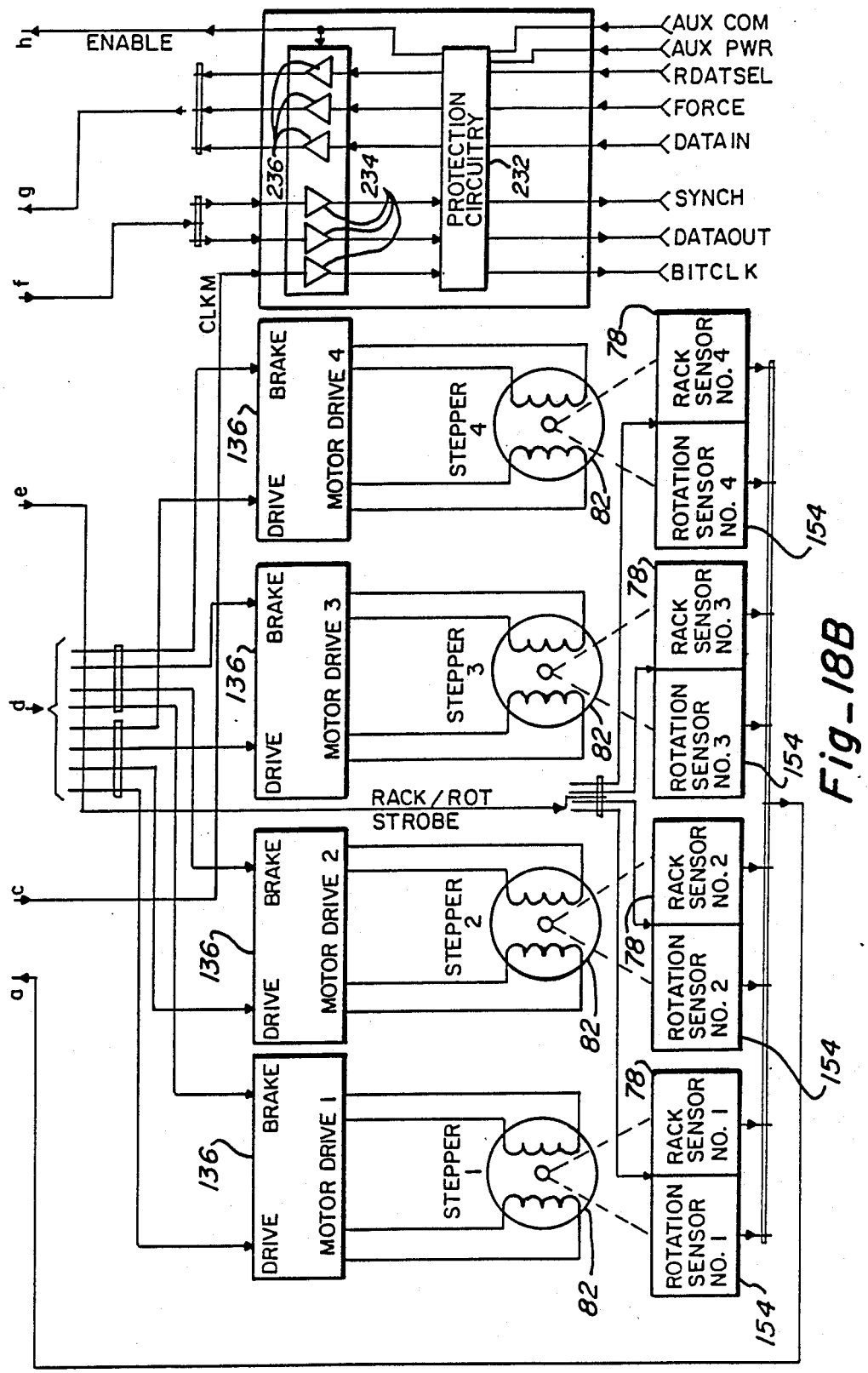
Fig_18B

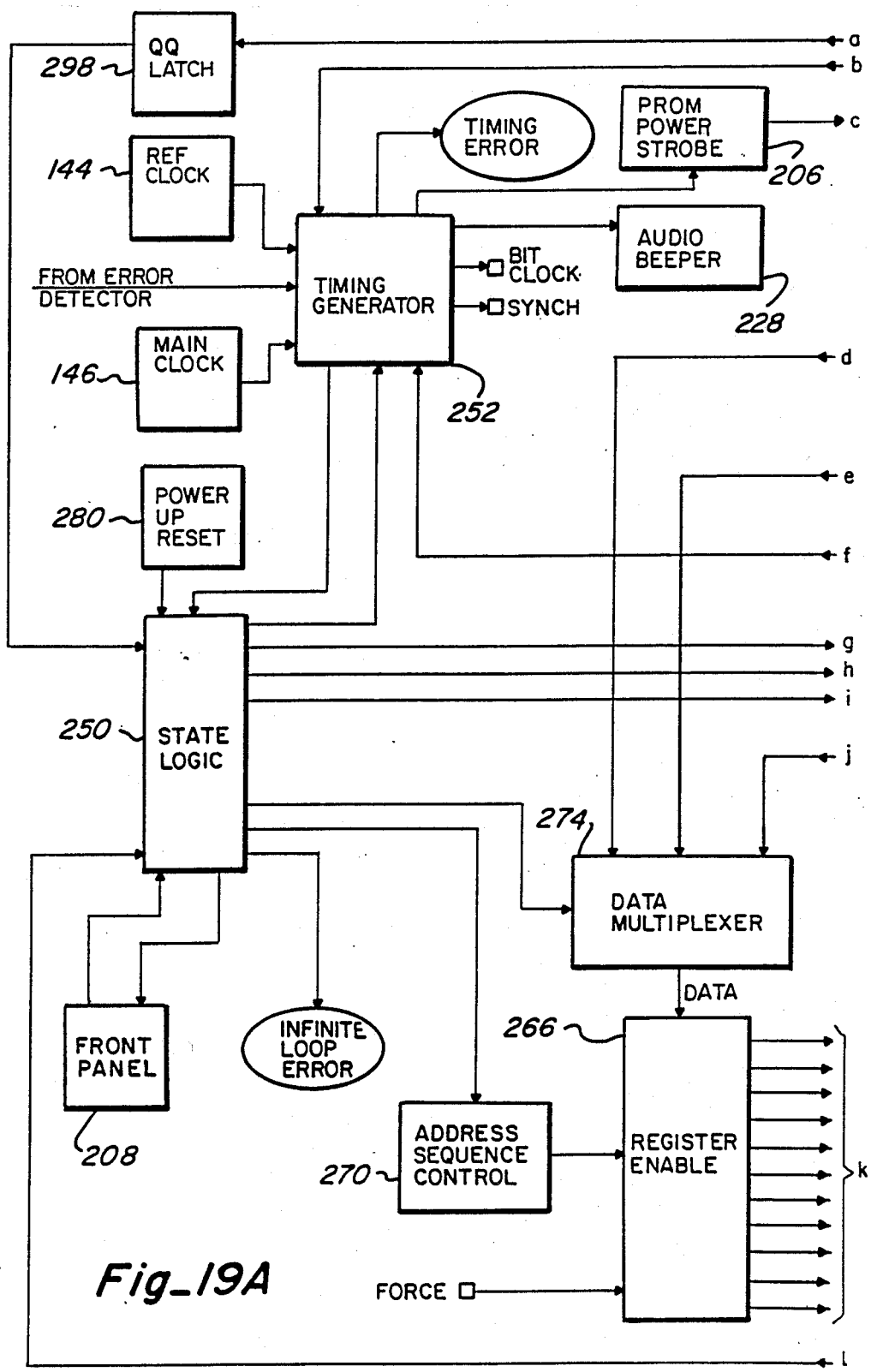
Fig_19A

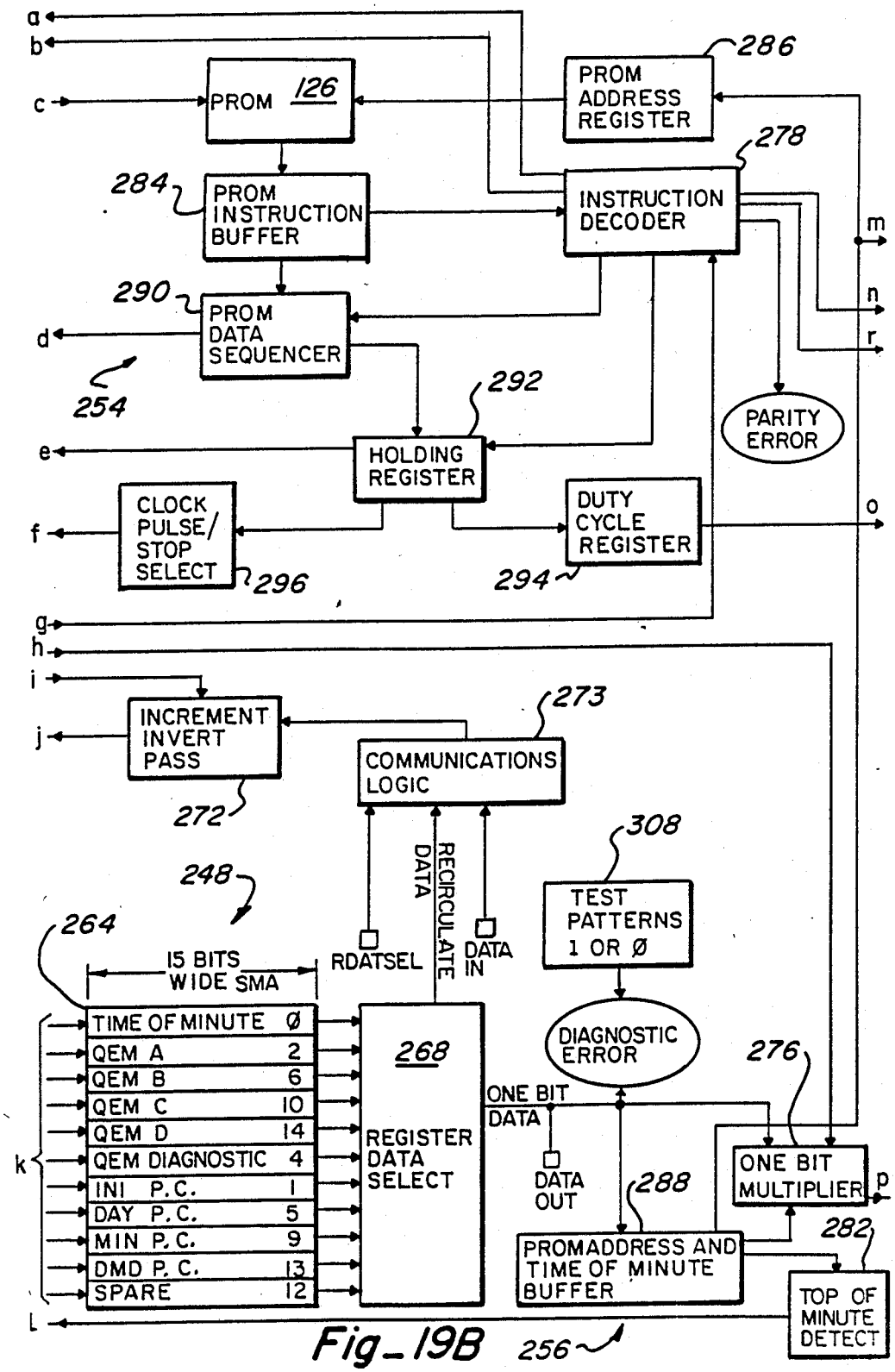
Fig_19B

Fig_21

FAILSAFE APPARATUS AND METHOD FOR EFFECTING SYRINGE DRIVE

RELATED APPLICATION

This application is a continuation-in-part of U.S. patent application Ser. No. 734,028, filed May 14, 1985, and entitled SYRINGE DRIVE APPARATUS AND METHOD, now abandoned.

FIELD OF THE INVENTION

This invention relates to an electromechanical drive apparatus and method, and, more particularly, relates to device and method for safely effecting syringe drive.

BACKGROUND OF THE INVENTION

The use of syringes to retain a fluid, such as a medicament, is well known. Devices and methods have also been heretofore suggested and/or utilized to control delivery of medicament from a syringe by controlling the movement of the syringe piston.

It is also known that the piston of a syringe can be driven by an electric motor through a linkage that can include a lead screw arrangement (see, for example, U.S. Pat. Nos. 4,529,401, 4,435,173 and 4,563,175) or a rack and pinion arrangement (see, for example, U.S. Pat. Nos. 3,395,704 and 4,532,460), and it has been suggested that a stepper motor might be utilized to drive a syringe piston (see, for example, U.S. Pat. Nos. 4,435,173 and 4,481,454). In addition, a stepper motor with reduced power consumption has also been heretofore suggested (see, for example, NASA Technical Briefs, Volume 8, Number 4, MFS-25119, Summer 1984), as has use of optical sensors to sense shaft or piston movement (see, for example, U.S. Pat. Mo. 4,475,666).

Prior devices and methods for controlling movement of the syringe piston have, however, not proved to be fully effective, at least for all intended purposes. Such prior known devices and/or methods have, for example, been ineffective in precisely controlling medicament delivery, have lacked the ability to deliver changing amounts of medicament over different time periods, have lacked safeguards against undesired use, have not been fully capable of safe and dependable operation, and/or have lacked simplicity of structure and/or operation.

SUMMARY OF THE INVENTION

This invention provides a substantially failsafe device and method for controlling delivery of fluid from a syringe. One or more syringes are positioned so that the piston of each syringe is caused to be precisely displaced to thereby safely delivery medicament from the syringe to a patient.

In the preferred embodiment, precise delivery of fluid from the syringe is effected using a disposable unit insertable into a drive unit, with the disposable unit including both the syringe and a rack preferably formed as a part of the piston.

A non-disposable unit is also shown for effecting precise delivery of fluid from a syringe and piston unit insertable into a drive unit so that the piston is secured to the rack of a rack and pinion arrangement provided in the drive unit.

In either case, however, piston drive is accomplished through an electromechanical arrangement that includes dual-redundant state machines and a plurality of error checks and data integrity verifications to facilitate failsafe operation.

It is therefore an object of this invention to provide an improved device and method for controlling delivery of fluid from a syringe.

It is another object of this invention to provide a substantially failsafe device and method for controlling delivery of fluid from syringes.

It is still another object of this invention to provide an improved device for controlling delivery of fluid from a syringe utilizing an electromechanical arrangement that includes dual-redundant state machines.

It is still another object of this invention to provide an improved device and method for controlling delivery of fluid from a syringe utilizing a plurality of error checks and data integrity verifications.

With these and other objects in view, which will become apparent to one skilled in the art as the description proceeds, this invention resides in the novel construction, combination, arrangement of parts and method substantially as hereinafter described and more particularly defined by the appended claims, it being understood that changes are meant to be included as come within the scope of the claims.

DESCRIPTION OF THE DRAWINGS

The accompanying drawings illustrate complete embodiments of the invention according to the best mode so far devised for the practical application of the principles thereof, and in which:

FIG. 1 is a perspective view of the syringe drive device of this invention shown with the protective casing in the closed position;

FIG. 2 is a partial front perspective view of the disposable syringe drive device of this invention shown with the protective casing in the open position and illustrating the disposable syringe assembly operatively placed within the casing;

FIG. 3 is a rear perspective view of the syringe drive device shown in FIG. 2 with the lid cut away for illustrative purposes;

FIG. 4 is a top perspective view of the syringe drive device as shown in FIG. 3 except that the disposable syringe assembly has been removed from the device;

FIG. 5 is a partial perspective view of the disposable syringe assembly shown in FIGS. 2 and 3 and illustrating the retaining clip locking feature;

FIG. 6 is a top view of the syringe drive device as shown in FIGS. 2 through 4 with various structures partially broken away to illustrate gearing for the rack and pinion drive assembly;

FIG. 7 is a top view of the syringe drive device with the lid removed and four syringes operatively positioned to illustrate different driven stages of the syringes;

FIG. 8 is a perspective view of the non-disposable syringe drive device of this invention shown with the protective cover in an open position and without syringes operatively positioned within the casing;

FIG. 9 is an exploded partial side view of the rack and connecting assembly for use with the non-disposable syringe device as shown in FIG. 8;

FIG. 10 is a partial side view of the rack and connecting assembly for use with the non-disposable syringe device as shown in FIG. 8 with the rack shown connected with the syringe piston;

FIG. 10(A) is a partial perspective view illustrating the rear section of the rack assembly;

FIG. 11 is a side view of the rack and connecting assembly as shown in FIG. 10 with the rack shown in position for releasing the piston;

FIG. 12 is a simplified layout schematic of the syringe drive unit;

FIG. 13 is a simplified layout schematic illustrating syringe drive and control;

FIG. 14 is a perspective view of an alternate embodiment of the syringe device using a hinged rack assembly;

FIG. 15 is an end view of another embodiment of the syringe drive device utilizing a one-way roller drive;

FIG. 16 is a series of timing pulses utilized to drive the stepper motor;

FIGS. 17A and 17B, taken together, form a block diagram of the now preferred electromechanical arrangement of the device of this invention;

FIGS. 18A and 18B, taken together, form an expanded block diagram of the electromechanical arrangement shown in FIGS. 17A and 17B;

FIGS. 19A, 19B, and 19C, taken together, form an expanded block diagram of a state machine, or gate array (master or slave), along with associated circuitry as shown in FIG. 18A.

DESCRIPTION OF THE INVENTION

Figure 18A:
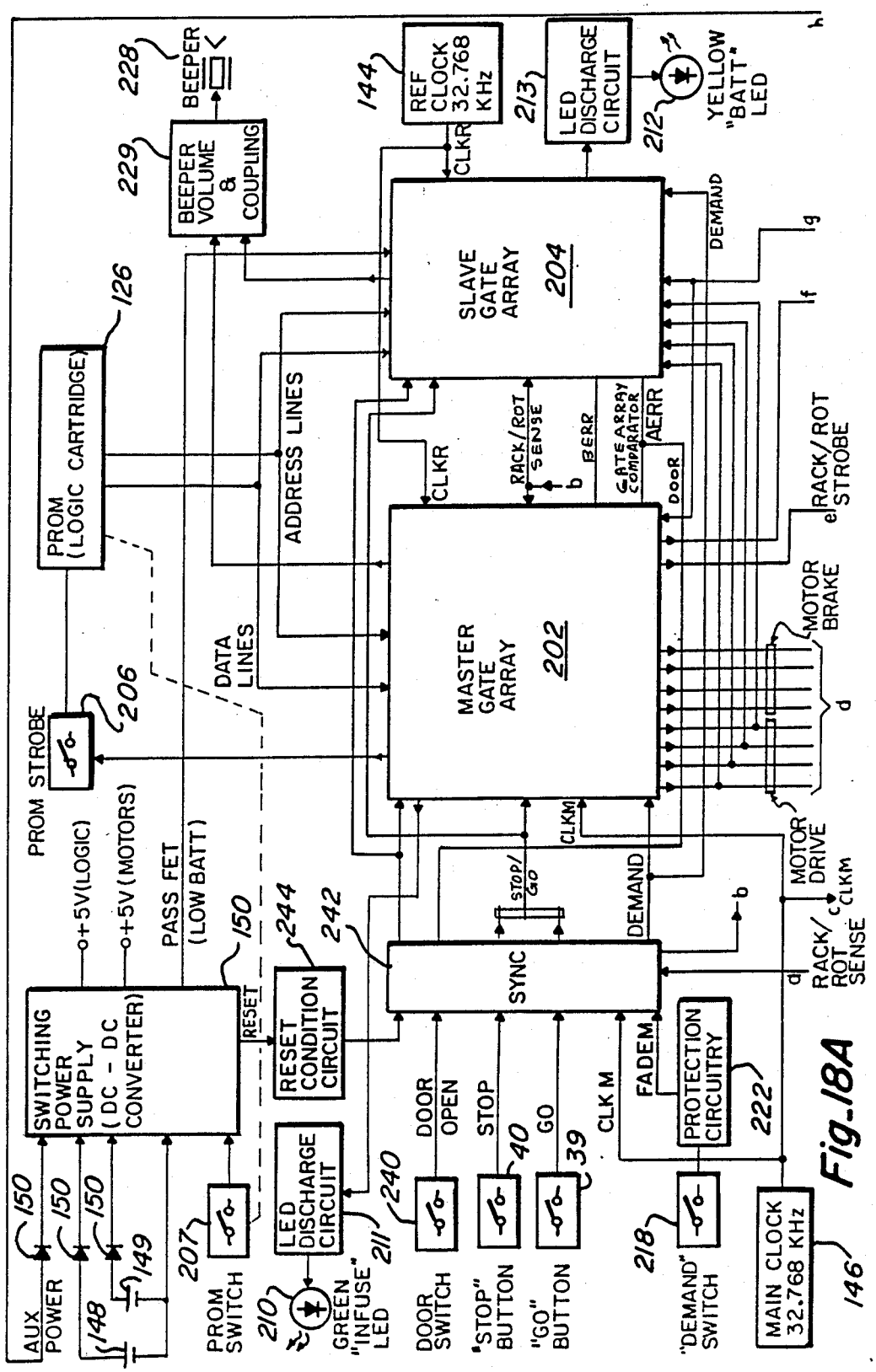

Referring now to the drawings, syringe drive 18 is shown in FIG. 1 within casing, or housing, 19. Casing 19, as best shown in FIGS. 1 through 4, includes a base, or bottom, portion 21 and a lid, or top, portion 22 that is hinged by hinges 23 at the rear side 24 of base portion 21. In addition, a retaining, or locking, mechanism 25 (see FIG. 5) is provided on mounting bracket 26 at the front side 27 of the base portion.

As best shown in FIGS. 1 through 3, a tab, or indicator, 29 is provided on rack 30 so as to be visible through the slotted openings 32 in the top 33 of lid 22. As shown in FIG. 1, indicia 35 are also preferably utilized at the side of each slotted opening 32 to indicate the amount of use of fluid dispensed from syringe 37 then being driven by rack 30.

As also indicated in FIGS. 1, 2, and 12, depressible start and stop buttons 39 and 40, respectively, are provided at front portion 27 of base portion 21 of the casing 19. In addition, a light emitting diode (LED) enable flasher indicator 42 is provided at base portion 21, and an information plate 43 is also provided at mounting bracket 26.

One embodiment of this invention is shown in FIGS. 2 through 7, and includes a disposable unit 45. Unit 45 includes syringe 37 and rack 30 both of which are mounted on retaining clip 47. Retaining clip 47 preferably receives and retains a plurality of syringes (four are indicated by way of example in FIGS. 1 through 7), and each syringe has a separate rack 30 connected with syringe piston, or plunger, 48 by means of connector 49 which receives centrally apertured piston 48 between disc 50 and end retainer 51 (see FIG. 6). Piston 48 has sealing lips 52 for engaging the inner surface of the syringe barrel, as is conventional.

As best shown in FIG. 5, retaining clip 47 includes a mounting wall 54 having a plurality of barrels 55 formed therein to receive the rear end portion 56 of each syringe. As also shown in FIG. 5, the rear end portion 56 of end syringe has arcuate lip portions 57 at opposite sides which are received in matching portions 59 of each clip barrel 55. After insertion and upon rotation (preferably about 90° of the syringe about its central axis), lip portion 57 rotates behind the end of the barrel, and is thereafter locked against movement with respect to the clip until the syringe is further rotated in either direction, so that the lips are again aligned with the matching arcuate portions of the barrel.

Mounting bracket 26 is attached to wall 54 and extends at one side of and parallel to syringes 37. In addition to snap fastener 25 at the top of mounting bracket 26 (for retaining the lid in the closed position), bracket 26 also has a snap fastener 61 protruding inwardly toward the syringes to enable the mounting bracket to be snapped into the base portion of the casing. In addition, bracket 26 preferably has a tamper-proof prescription label base 43 for receiving, as the information displayed, an indication of the prescription for medicaments to be included in the syringes retained by the clip.

Rack 30 includes an elongated T-shaped beam, or bar, 63, the upper, horizontally extending portion 64 of which has indicator 29 at the rear edge thereof, and the lower, vertically extending portion 65 of which has teeth 67 therein at one side 68. As can be appreciated from FIGS. 3, 5 and 6, teeth 67 are relatively small and fine to better control the longitudinal movement of the beam. As shown in FIGS. 2 and 6, a series of distinguishable strips 70 are provided at side 71 of vertical portion 65 of beam 63 to sense beam positioning, as brought out more fully hereinafter.

As best shown in FIGS. 2 through 4, disposable unit 45 is inserted onto base 21 at the top 73 thereof so that the syringes 37 are received in indentions 74 as mounting bracket 26 is snapped into place centrally of the base at the front thereof.

When disposable unit 45 is snapped into position, teeth 67 of each rack 30 engage pinion, or driving, gear 76, which gear extends above top 73 of the base portion of the casing. As also shown in FIGS. 4 and 6, vertical portion 65 of beam 63 extends between driving gear 76 and a pair of guide pins 77 to constrain movement of beam 63 in opposite longitudinal directions when being driven by pinion gear 76. As also shown in FIGS. 4 and 6, optical sensor 78 is positioned adjacent to guide pins 77 (and thus adjacent to side 71 of vertical portion 65 of beam 63) to sense the positioning of the optically distinguishable strips 70 on side 71.

Each rack 30 is independently driven by a separate driving unit 80, as best shown in FIG. 6. As shown, a series of gears 81 are positioned between pinion gear 76 and stepper motor 82 (as indicated in FIGS. 6 and 13) for enabling precise movement of the rack mechanism 30. As also indicated in FIG. 6, each driving unit 80 is mounted in a separate gear box 84, which gear box is positioned within base 21 of the casing below top 73.

FIG. 7 illustrates that the pistons 48 of the plurality of syringes 37 are independently driven through separate gearing 81 and separate pinion gear 76. As shown, each gear box 84 is mounted below and in line with the path of travel of beam 63 as beam 63 drives the associated piston 48 from a retracted position (at the rear of the syringe) to an extended position (at the front of the syringe) during which movement the fluid in the syringe is expelled, or discharged, from the syringe.

A non-disposable embodiment 88 of the syringe drive device of this invention is shown in FIGS. 8 through 11.

As indicated in FIG. 8, non-disposable embodiment 88 is similar to disposable embodiment 18 (as shown in FIGS. 2 through 7), except that rack 90 is mounted within the casing.

As indicated in FIG. 8, rack 90 includes indicator 29 which is visible through the slots 32 when the lid 22 of casing 19 is in the closed position (as shown in FIG. 1).

Rack 90 includes a beam, or bar, 91 having an upstanding shoulder 92 at the rear end portion (which shoulder has indicator 29 mounted at the top thereof). As indicated in FIG. 8, beam 90 has teeth 93 on one side wall.

As shown in FIG. 9, beam 91 preferably includes a central strip 94, which strip is within outer portion 95 of the beam. The forward end 96 of outer portion 95 of beam 91 is adapted to receive tip 97, which tip engages piston 98 of syringe 100.

Tip 97 has a disc 102 thereon that has a rearwardly facing annular connector 103 extending rearwardly therefrom. Connector 103 has a lip 105 thereon, so that as connector 103 is inserted into annular groove 107 (which groove has an annular shoulder 108) at the forward end 96 of beam 91, connector 103 is snapped into the annular groove, as indicated in FIG. 10. Alternately, the annular connector could have an inwardly directed lip which snaps over an outwardly directed shoulder on end 96 of beam 91.

A smaller disc 110 (i.e., smaller relative to disc 102) is parallel to and spaced forwardly of disc 102 by spacer 111 and terminates in guide 112 which extends forwardly of disc 110 for engaging piston 98. Disc 110 and guide 112 are inserted into piston 98 of the syringe/piston unit, as shown in FIG. 10 when the syringe is operatively positioned on the non-disposable unit. In this embodiment, only the syringe/piston unit is inserted into and removed from the syringe/piston unit.

As indicated in FIGS. 10 and 11, outer portion 95 of beam 91 can be retracted with respect to inner portion 94 to enable release of the rack from a syringe/piston unit. As shown best in FIG. 10(A), a gripping ear 114 is provided on outer portion 95 and gripping ear 115 extends extends through slot 116 so that ear 115 is connected with inner portion 94 of the beam. As the ears are moved toward one another, as indicated in FIG. 11, this causes the outer portion 95 to be retracted and pulls outer end 96 out of engagement with connector 103 of tip 97.

The driving mechanism for embodiment 88 is the same as shown in connection with the disposable unit of FIGS. 2 through 7 (i.e., pinion gear 76 meshes with teeth 96 of beam 91 to control longitudinal movement of the beam from the piston retracted position to the piston extended position, which movement of the piston effects medicament delivery from the syringe.

As indicated in FIG. 8, a cover 117 is provided for covering the pinion gears 76 and guide pins 77. While not specifically shown in FIG. 8, beam 91 preferably also has distinguishable strips 70 thereon with strip sensor 78 also being within cover 117.

A simplified layout schematic of the syringe drive device (non-disposable or disposable) is shown in FIG. 12. As shown, a syringe pack 120 is provided (although each syringe may, if desired, be individually provided), with each syringe containing the predetermined amount of the desired medicament to be dispensed. Pack 120 (or the individual syringes) is placed in the dispensing rack (i.e., the syringes are received in indentations 74 in the top of the base portion of the drive unit) so that the drive modules 121 (i.e., the pinion gears and associated gearing to the stepper motor) drive the piston of each syringe to deliver medicament as needed. The indicators visible at the top of the unit give a visual indication of the amount of medicament delivered at any time from any syringe.

As also indicated in FIG. 12, the device is battery powered, by means of batteries 122, and preferably includes indicators (LEDs) 124 to indicate satisfactory battery charge.

As also indicated, the syringe drive unit of this invention is controlled by pre-programmed memory unit 126, which unit is preferably a programmable non-volatile logic device, such as a PROM device. It is necessary that unit 126 be inserted into the device for operation of the device. The pre-programmed memory unit is externally programmed to establish the time and amount of medicament to be delivered by each syringe and controls the operation of the drive unit so that the exact amount is independently delivered from each syringe at the exact required time. The pre-programmed memory unit is preferably programmed remote from the drive unit as shown in U.S. Pat. No. 4,676,776 owned by the assignee of this invention.

In addition, a history 128 of medicament delivery is made and stored for use in prescribing further medicament delivery, a beeper 130 is provided for alerting purposes, and remote demand option 132 can also be provided to allow a patient to control medicament delivery when, and to the extent, allowed by the pre-programmed memory unit 126.

As indicated by the simplified schematic of FIG. 13, a state machine 134 controls operation of stepper motor 82 through motor drive 136.

A state machine is a logic network whose output state is determined by the present state of its input and the state of data currently being read from memory. A combinational logic could be utilized in lieu of a state machine. While a microprocessor could also be utilized in lieu of a state machine, it is not preferred due to safety and/or other factors.

While only one stepper motor is illustrated in FIG. 13, it is to be realized that a separate stepper motor is provided for each rack 30 utilized. State machine 134 provides a pulse output through motor driver 136 to each stepper motor so that the drive is thus accomplished as a pulse device (rather than as a DC device). Each pulse causes the stepper motor to advance by increments, which motion is imparted through the associated gearing (within gear box 84) to pinion gear 76. As indicated in FIG. 13, a mechanical ratchet 138 is provided between stepper motor 82 and the gearing within gear box 84 to assure one-way drive. Rotation of pinion gear 76 causes longitudinal movement of beam 63 (or beam 91 if a non-disposable unit) to thus move the syringe piston a precise distance to thereby deliver the exact amount of medicament prescribed.

A stepper motor is utilized in this invention for reasons of safety in the case of an accidental conductive path forming between the power supply of the device and the motor, which with DC motors causes uncontrolled motion. A stepper motor, on the other hand, requires clearly defined pulses in order to operate. Stepper motors have not been found to be fully satisfactory for use with battery-operated syringe drive devices, however, since one disadvantage of such motors heretofore known to have been utilized has been high power consumption.

By this invention, the safety benefits of the stepper motor have been achieved by utilization of power efficient means for driving the stepper motor which has allowed use of the stepper motor without requiring high power consumption and thus has permitted use of the stepper motor with a battery operated device.

The power efficient means for operating the stepper motor is illustrated by the pulse timing illustrations of FIG. 16. The pulse timing illustrated in FIGS. 16(A) and 16(B) are manufacturer drive pulse recommendations (FIG. 16(A)), and pulses as utilized in connection with a stepper motor as reported in NASA Technical Briefs, Volume 8, No. 4, MFS-25119, Summer 1984 (FIG. 16(B)). The conventional step drive shown in FIG. 16(A) is powered on between steps and energy efficiency is low, while the drive is partially powered on between steps in the drive shown in FIG. 16(B) with energy efficiency being moderate.

FIG. 16(C) illustrates pulses in a ballistic drive utilizable in conjunction with a unidirectional rachet presenting known inertia mounted on the motor shaft and including a pawl for establishing the direction of rotation. FIG. 16(D) illustrates drive pulses that consume less energy than those previously shown in FIG. 16 and which embody a dynamic braking effect. FIG. 16(E) illustrates drive pulses allowing precise design of energy consumption and force development by the motor by means of duty cycle programming of the pulses. All of the drive pulses shown in FIGS. 16 C, D, and E can be utilized in this invention, to provide high energy efficiency, with the drive pulses as shown in FIG. 16(E) being now preferred.

The pulse parameters are chosen in view of the desired inertia presented to the motor and in view of the maximum force to be allowed for any particular application.

As also indicated in FIG. 13, an internal memory check is provided by memory check unit 140, and a clock check is provided by clock check unit 142, which unit may be connected to clocks 144 and 146. In addition, batteries 148 and 149 are connected to power the device through a diode type network 150, and a mini-battery 151 is provided for back-up. A control strip 153 is also provided for connection with the state machine.

Strip sensor 78 is positioned adjacent to side 71 of beam 63 to sense positioning of strips 70 thereon. As indicated in FIG. 13, the output of sensor 78 is provided to state machine 122. In addition, rotation of the gearing within the gear box 84 (which gearing is connected with pinion gear 76 to cause movement of the rack and syringe piston) is sensed by rotation sensor 154 (which sensing can be accomplished, for example, by placing holes in an associated gear 155 and providing a light generator at one side and a sensor 154 at the opposite side). The output from sensor 154 is also provided to state machine 122. By thus sensing longitudinal movement of the beam and gear rotation, positioning control is enhanced and verified.

An alternate embodiment 158 is shown in FIG. 14 for driving the syringe piston. As shown, a hinged rack 160 is provided to apply drive to the piston 47. To accomplish this type of drive, a plurality of rack sections 162 are provided each of which is connected with its adjacent section through a hinge pin 164. One end 166 of the thus formed hinge assembly is connected with the piston 47, and the teeth 168 on each section 162 are sequentially brought into engagement with gear 170, which gear is in engagement with worm gear 172 rotated by stepper motor 82.

In addition, while an external plug 174 is indicated, internal battery operation can be utilized in the same manner as described herein above with respect to the other embodiments described herein.

Operation is essentially the same as with the previously described embodiments, except that the driving mechanism can be adjacent to the syringe and less longitudinal space is required due to hinging of the rack.

Another drive embodiment 178 is shown in FIG. 15. As indicated, precise rotation of shaft 180 is provided by a one-way (clockwise as indicated) roller device unit 182. In this embodiment, rotation of the shaft is accomplished using balls 184 engaging the shaft. Each ball 184 is within a channel 186 having a slot 188 therein. Slot 188 is a longitudinally extending slot that is sufficiently wide to allow the ball to partly protrude therethrough so that the ball engages the shaft. In addition, each ball 184 is biased toward the end of the channel by a spring 190.

Clockwise rotation of the shift is permitted since the ball is being rotated by such movement in a direction away from the restraining wall of the channel. Counter-clockwise rotation of the shaft is precluded, however, since attempted rotation of the shaft in this direction forces the ball into the restraining wall of the channel. Through use of this type of drive, rotation of shaft 180 controls movement of the syringe piston and no ratchet mechanism is required.

In operation of the disposable device of this invention, the disposable unit, with a predetermined amount of medicament in each syringe to be utilized, is loaded into the drive device while the lid of the casing is in an open position, by positioning the syringes in the syringe indentations at the top of the base portion as the mounting bracket is snapped into place at the front of the base portion. When so loaded, the teeth on the rack are brought into engagement with the pinion. The casing lid is then closed and locked by the mounting bracket snapping into the lid of the casing at closing. After insertion of a pre-programmed memory unit into the casing (through a closeable aperture (not shown) in the bottom of the casing), the unit is ready for use in dispensing medicament to a patient. In use, each syringe is connected with the patient in conventional fashion and medicament is thereafter delivered to the patient under the control of the pre-programmed memory unit.

When the medicament in the syringe (or syringes) is depleted, the disposable unit is removed from the drive device and discarded. If needed, a new unit can then be placed in the drive device for continued operation. Such a new unit can contain the same or different medicaments as determined to be needed by the patient's history.

The non-disposable unit operates in essentially the same manner as does the disposable unit, except that only the syringes and pistons are introduced into the unit (either individually or as a pack) with each syringe being positioned on the base unit and each piston being then connected with a separate rack. After use, each piston is disconnected from the rack, and the syringe then taken from the base unit and discarded.

A now preferred embodiment 200 for the electromechanical arrangement of the device of this invention is shown by the block diagram of FIGS. 17A and 17B. The mechanical drive arrangement, as indicated in FIG. 17B, is the same as that described hereinabove with respect to FIGS. 12 and 13, and includes a syringe pack 120 including four syringes 37. The piston 48 of each of each syringe is secured to a different one of four beams, or racks, 63, and each rack 63 engages an associated pinion gear 76 the rotation of which controls longitudinal movement of the associated rack to thereby effect medicament delivery by causing precise movement of the associated piston upon rotation of the pinion gear, as is more fully described hereinabove.

As also indicated in FIG. 17B, sensor 78 senses longitudinal movement of the associated rack, while rotation sensor 154 senses rotation of the gears of gear drive 81 causing rotation of the associated pinion gear. The two motion detectors 78 and 154 provide feedback signals to the state machine so that proper mechanical movements can be verified during fluid delivery.

Rotation sensor 154 has three perforations and is located on a selected stage of the gear box. A strobed optical interrupter senses presence or absence of the perforations, and the state machine determines whether the wheel is rotating properly.

A strobed optical reflective sensor is located near the output pinion gear. This sensor reads the presence or absence of reflective stripes on each syringe plunger (rack), and logic within the state machine determines whether the plunger is moving properly. There are 12 reflective stripes located on each plunger, representing a fluid delivery of approximately 30 cc of fluid.

The rotation sensor provides a motion check every 64 motor steps, or approximately 96 microliters of fluid delivered. The plunger sensor provides a check of actual syringe plunger movement every 1024 motor steps or approximately 1.54 milliliters of fluid delivered. These sensors are used to indicate a stalled stepper motor, as might occur if the IV line is occluded. Under normal conditions, a stalled stepper motor is signalled within 96 microliters of missing fluid delivery by the rotation sensor. The rotation sensor is thus able to indirectly determine patient line overpressures.

A stepper motor 82 is utilized to drive the pinion gear through gear drive 81, and each stepper motor is driven by stepper motor drive electronics 136 (see FIG. 17A). Stepper drive electronic circuits 136 are hybrid circuits which contain two transistorized full H bridge drive circuits which have been designed to draw negligible current when the stepper motor is powered down. The bipolar transistors and resistors on each hybrid have been assembled using microminiature surface mount components, and then conformally coated so that a very small package results. The hybrid circuits allow the two-coil, bipolar stepper motor to be driven in a conventional fashion, but also allows the motor to be braked after each step by effectively shorting out the motor coils through the hybrid.

Stepper motors 82 are preferably 15° permanent magnet units having 24 detents per revolution. The stepper motors are caused to take a single step, braked as described above, and then powered down until the next step is required. Ordinarily, a stepper motor would tend to back up under load if power is removed in between steps. The gear drive utilized (having an overall ratio of 267:1 is designed for high efficiency and includes a special miniature ratchet on the first stage so that step position is not lost in between steps. This technique allows the stepper motor to be power efficient at the low step rates used in the device of this invention.

The stepper drive voltage which originates in the master state machine, or gate array, is a switched waveform having a duty cycle settable from PROM instructions. This technique allows the energy content of a motor step to be set from a computer during remote programming of the PROM cartridge so that the load stall point of the step motor can be set by the computer operator. Variable motor drive force, in addition to rotation feedback, forms the basis of infusion line overpressure control.

Using a stepper motor rather than a DC motor is intrinsically safer technology because a direct short from the battery to the motor cannot result in fluid delivery since the step motor runs only if properly timed pulses are present.

The electronics utilized for the device shown in FIGS. 17A and 17B is similar to that of the device shown in FIG. 13, except, primarily for the inclusion of dual-redundant state machines 202 and 204 (a single state machine is identified by the numeral 134 in FIG. 13) one of which is a master state machine (202) and the other of which is a slave state machine (204). Both state machines are preferably identically configured and may be referred to as gate arrays. In addition, both state machines include nine error checks and verifications as brought out more fully hereinafter.

As indicated in FIGS. 17A and 18A, power for the device is supplied through a pair of 9 volt batteries 148 and 149 connected through diodes 150 (see FIG. 18A) so that either can operate the device by providing power to power supply 150 (which identified as a diode type network in connection with FIG. 13), and a pair of clocks 144 and 146 (each operating at a frequency of 32.768 KHz) are connected with each state machine 202 and 204 with clock 146 being the main timing clock and clock 144 being a reference timing clock. If either clock fails or if the clocks disagree (beyond a predetermined threshold), pump (delivery unit) operation is terminated and an alarm is sounded.

Programmed memory 126 (identified in FIG. 17 as a PROM profile cartridge and in FIG. 18A as a PROM logic cartridge) is likewise connected with both state machines 202 and 204, and an electronic switch (a power FET) 206 is provided between master state machine 202 and PROM cartridge 126 so that the PROM cartridge is powered on for only 30 microseconds for each READ operation. As indicated in FIG. 18A, PROM switch 207 is also provided to assure that the drive circuitry cannot be operated unless the PROM cartridge is in its proper operating position.

Control panel 208 is similar to that of control panel 153 shown in FIG. 13 except in providing a light emitting diode (LED) 210 acting through LED discharge circuit 211 (as indicated in FIG. 18A) to indicate infusion, and a light emitting diode (LED) 212 acting through LED discharge circuit 213 (as indicated in FIG. 18A) to indicate a battery problem. Control panel 208 also includes enable switch 214 which must be depressed in addition to start or stop switches 39 and 40. A demand unit 216 is also provided with start switch 218 and enable switch 220 (which must be depressed along with switch 218) as indicated in FIG. 17A.

Demand switch 218 is operable only if the PROM cartridge has been programmed to accommodate such use and a demand delivery schedule established. If so, fluid delivery associated with the demand switch will start to flow within one minute after requested. It is possible to provide various safeguards such as, for example, to provide a lockout time so that fluid will not flow until a certain time has passed before a second demand requirement will be acted upon by the device (demand programs must be less than three hours total length in this device). In addition, protection against overvoltage is provided by protection circuitry 222 as indicated in FIG. 18A.

As also illustrated in FIG. 17A, master/slave comparison lines 224 and 226 are connected between the state machines and an audible indicator (beeper) 228 (acting through beeper volume and coupling unit 229 as particularly indicated in FIG. 18A) is also connected between the state machines. As also illustrated, both state machines are also connected with external communication port 230.

The master state machine is responsible for receiving flow rate data from port 230 and to convert it to stepper motor drive signals, just as when utilizing a PROM cartridge. The slave device receives the same data from the port and calculates both stepper drive signals and effective PROM addresses. If a discrepancy should develop between the master and slave, as with PROM input, a miscompare error will be generated.

When operating from the communications port, power is obtained from the port electrical connection instead of the internal batteries 148 and 149. Presence of a 9.5 volt–11 volt power supply at the port connector enables the port data lines. As indicated in FIG. 18B, all interconnect lines between the device and port 230 are protected against overvoltage (electrostatic discharge) conditions by protection circuitry 232 and diodes 234 and 236 are provided between the protection circuitry 232 and the state machines.

It should be noted that the basic architecture of the dual state machines and independent checks provided within the state machines allows passive data monitoring as well as register modification to share the basic safety design of the system. That is to say, if either passive monitoring or register modification results in a data format which a state machine doesn't understand, a hard error will normally result.

However, the communications port has complete freedom to change the data numbers (Q, E, and M) and the motor drive duty cycle at will, so that qualitative monitoring for safety must take place within the smart interface if register modification is undertaken.

The communications port inputs shown in FIG. 18 are as follows: Bitclock is the 32.768 KHz main clock; Data Out is the state machine's one bit serial data stream which has been selected from the shiftable memory array by surrounding logic; Synch is Bitclock divided by 240 and is synchronous with a fetch of register 0, the time of minute counter, and undergoes one complete cycle every two machine cycles, or 240 bits (note that by reading the serial data present in the data line outline immediately following Synch, time of minute can be determined and the unique time of minute indicating start of the actual fluid delivery period (mode 4) can be trapped, and Bitclock can be counted from that time which allows synchronization to any machine state within the delivery period for read-only, or data modification purposes); Data In allows serial data to be written to the one bit data bus provided the Rdatsel line is made active, with the register being written to depending on the exact time state within the machine, as determined by reading the time of minute counter and counting Bitclock from that time; Rdatsel enables the Data In line; Force allows modification of the four program counters (INI, Day, Dmd, and Min); and Auxiliary Power enables the communications port and at the same time powers the entire infusion pump (a nominal 10 volts being required).

As can be appreciated from FIGS. 17A and 17B and 18A and 18B, master and slave state machines 202 and 204 are controlled by PROM profile cartridge 126 to provide for controlled operation of the device. Each state machine is an application specific integrated circuit and, more specifically, is a CMOS gate array which as a part thereof includes a plurality (nine as shown) of error checking and data integrity verification circuitry.

The error checking circuitry monitors control signals and terminates pump operation if erroneous states appear, while the data integrity verification circuitry inserts known data patterns into control paths and checks to see whether known expected results appear so that, if the expected result does not appear, operation of the device is terminated and an alarm sounded.

In this invention one state machine (master state machine 202) is used as the primary unit for causing operation of the device under the control of PROM cartridge 126, while the other state machine 204 is used in a quasi-redundant manner to virtually assure detection of any faults in the system so that the system thus operates substantially failsafe.

Both state machines receive the same data from PROM profile cartridge 126, and cartridge 126 controls the multi-channel (four as specifically indicated) flow profile operation, and both state machines process the data identically in parallel to produce identical motor step drive signals if no errors have occurred in either of the state machines. If different motor drive signals are produced, or if different addresses are calculated by the state machines at the same moment of time from the PROM cartridge, then a miscompare error signal is generated by either or both state machines and this will cause termination of operation of the device and will cause an alarm to be sounded. A manual reset is required to restart the device. The comparison error is conducted on the two identical, redundant, wired-or miscompare lines 224 and 226 shared by the state machines.

As indicated in FIG. 18, a door switch 240 is also provided to cause the device to terminate operation and sound an alarm if the syringe access door is open. When the door is closed, operation will resume and the alarm will no longer sound. Door switch 240 is connected to the state machines through sync unit 242.

Reset condition circuit 244 is also connected through sync unit 242 to the state machines, and the state machines are simultaneously reset so that the fluid delivery profiles is caused to begin at its starting location, upon receipt of a new signal (which can occur, for example, by insertion of new batteries or for manual operation of a lever located on the PROM cartridge socket).

Coordinated four channel fluid delivery profile data (assuming four channels are to be utilized) is remotely encoded into the PROM cartridge by a computer (programming means) and read by both master and slave state machines in order to generate appropriately timed stepper motor commands for each of the four delivery channels. The medium of encoding and decoding between the computer and the delivery unit, or pump, is the compiled instruction set which they hold in common.

More particularly, master state machine 202 establishes operation of the application device (i.e., the pump). A state machine is a digital logic device which has a finite and repeatable number of operations it can perform, according to the interconnection of its registers and logic gates.

The dual state machines set forth in FIGS. 17A and 18A are designed to receive operating instructions from PROM cartridge 126. The PROM cartridge, in turn, is programmed by the remotely situated computer which contains within its software a logical equivalent of the state machine.

The computer and state machines have a common language of instructions (32 for example as used in a specific embodiment of this invention) which the state machines can decode and then act upon. The computer places these instructions into a program which it then compiles into a list of as many as 16,384 eight bit words which are burned into the PROM cartridge carrying the program from the computer to the pump.

The state machines are organized around minutes. Once each minute each state machine reads the PROM cartridge for fluid delivery instructions for that minute only, and thus the machines know what fluid to deliver for only a minute at at time, and the PROM cartridge must be read again for the next minute's instructions.

There are four key events or modes that the state machines enter in the course of a minute. These four modes are executed sequentially every time a new minute begins, and together they occupy the whole minute and cause the state machines to carry out all required functional tasks, including the output of step commands (from the master state machine) which cause the delivery of fluid.

Dual-redundant state machines are included in the device of this invention and the primary purpose of the slave state machine 204 is for extensive error monitoring and verification concurrent with operation of master state machine 202. Slave state machine 204 checks passively to see if incorrect data is produced.

The four basic modes of operation of the state machines from start of minute to end of minute are as follows:

The new minute's program is next read from the PROM cartridge in the Fetch Instructions mode. Generally speaking, complete programming information for a minute can be accomplished in less than 25 instructions but time is allotted for as many as 521 instruction cycles. Each PROM cartridge word includes parity checking, and incorrect parity results in a hard error which will cause an alarm which can only be cleared by resetting the state machine. The fetch mode lasts from 7.32 ms to 1.908 seconds depending on the length of the program for that minute. During fetch mode four functionally different "programs" are executed sequentially in order to set up the state machine for that minute's delivery. These include the following:

The Initialization (INI) program passes information such as step motor duty cycle, stop or go, test pattern 1 or 0, unique patient ID number, and audio beeper commands to the state machine (it must run each minute, although it does not have to pass all the information listed herein);

The Day (Day) program can change fluid delivery on an hourly basis for up to 31 days (it runs only if programmed by the computer);

The Minute (Min) program can change fluid delivery on a minute-by-minute basis for up to 24 hours (it runs only if programmed by the computer); and The Demand (Dmd) program is a unique delivery schedule for any channel with up to three hours duration (it runs only if programmed by the computer and if a Demand program is present for a particular minute, it will cause its channel to delivery fluid in accordance with its instructions only if a patient activates the Demand switch).

At the conclusion of the Fetch Instructions mode, the state machine runs a verification test on a large portion of its own circuitry. The test utilizes the new delivery data just obtained during the fetch mode, inverting and routing it through circuitry which should not produce any outputs if the state machine is functioning properly.

| | | BASIC MODES | |
|---|---|---|---|
| CLEAR Q MODE | FETCH INSTRUCTIONS MODE | TEST STATE MACHINE MODE | DELIVERY AND DIAGNOSTIC TEST MODE |
| 4 Machine Cycles | 2–521 Machine Cycles (Depends on program) | 4 Machine Cycles | 15,855–16,374 Machine Cycles (Depends on program) |
| 14.65 ms | 7.32 ms to 1.908 sec (Depends on program) | 14.65 ms | 58.06 sec to 59.96 sec (Depends on program) |
| What Happens | What Happens | What Happens | What Happens |
| Set all Channel Deliveries to Zero | Read This Minute's Instructions From PROM Cartridge Initialization Instructions Day Instructions Minute Instructions Demand Instructions | Verify Proper Operation of Major Parts of The State Machine | Pulse Stepper Motors (Deliver Fluid) Concurrent Verification For Major Parts Of The State Machine |
| Why | Why | How | How |
| A Default Safety Measure | Prepare the State Machine For This Minute | Route Inverted Delivery Data Through State Machine & Look For Known Results | Compare Hardwired "Pattern 0"or "Pattern 1" With Prom Data Placed in RAM Diagnostic Register |

At the conclusion of a previous minute's fluid delivery, the state machine first sets its fluid delivery ("Q") registers to zero so that fluid cannot be delivered from that time on unless new instructions are successfully reads from the PROM cartridge. This Clear Q mode operation takes 14.65 milliseconds.

If the test fails, a hard error state is entered. The test mode takes 14.65 milliseconds to complete. The first three modes last from 36.62 ms 1.937 seconds from the start of a new minute, depending on the length of the program for that minute. During this time fluid delivery does not occur.

The earliest that fluid delivery can occur is 1.937 seconds after the start of a new minute. The remaining 58.06 seconds in a minute (at maximum flow rate) are devoted to fluid delivery and concurrent state machine verification testing of a type different than found in the Test mode. Fluid delivery may occur almost continuously during the delivery mode if the programmed delivery for that minute is high, but fluid delivery may occur sporadically throughout the remainder of the minute for smaller required deliveries (the sporadic or apparently random quality of fluid delivery is a consequence of the hardware circuitry and algorithm employed by the state machine to produce motor step commands from the data which it has retrieved from the PROM).

Throughout the Delivery Mode, tests are run which utilize a portion of the shift register memory array 248 contained within the state machine. Each minute during Fetch Mode a test bit pattern, which has been intentionally placed in the PROM cartridge by the computer, is retrieved. During Delivery Mode, this pattern is compared with one of two patterns (Pattern 1 or Pattern 0) hardwired into the state machine. Pattern 1 and Pattern 0 are alternated on alternate minutes for this test. If the test fails, a hard error is issued.

During the Delivery Mode, step commands are output and both the rotation sensor and syringe plunger move in response to these commands. The state machine has a portion of logic which expects to see alternating high and low signals from the feedback sensors in precise relationship to the number of step commands issued. If either sensor emits the wrong logic level when the opposite is expected, the state machine issues a soft error alarm requiring the operation to press STOP and then GO to restart the pump.

There are four effective error types. They are hard error, soft error, miscompare error (internal), and miscompare error (external).

A hard error indicates that the error machine has detected an internal data malfunction, and the pump must be investigated further before reuse. A hard error is cleared by resetting the state machine, however, the fluid delivery profile begins from its starting location in this case.

A soft error results from the motion feedback detectors and indicates that incorrect syringe plunger or gear drive motion has been detected. The most likely cause is an occluded IV line. A soft error is cleared by pressing STOP and then GO from the control panel.

An internal miscompare error is a hard error generated by a discrepancy between the master and slave state machines. It is indicated by a low logic level on one of the two miscompare lines. It is treated as a hard error.

An external miscompare error is generated by pulling either miscompare line low, external to the master or slave state machine. The pump enters an alarm state which cease as soon as the short is removed from the miscompare line.

Figure 19C:
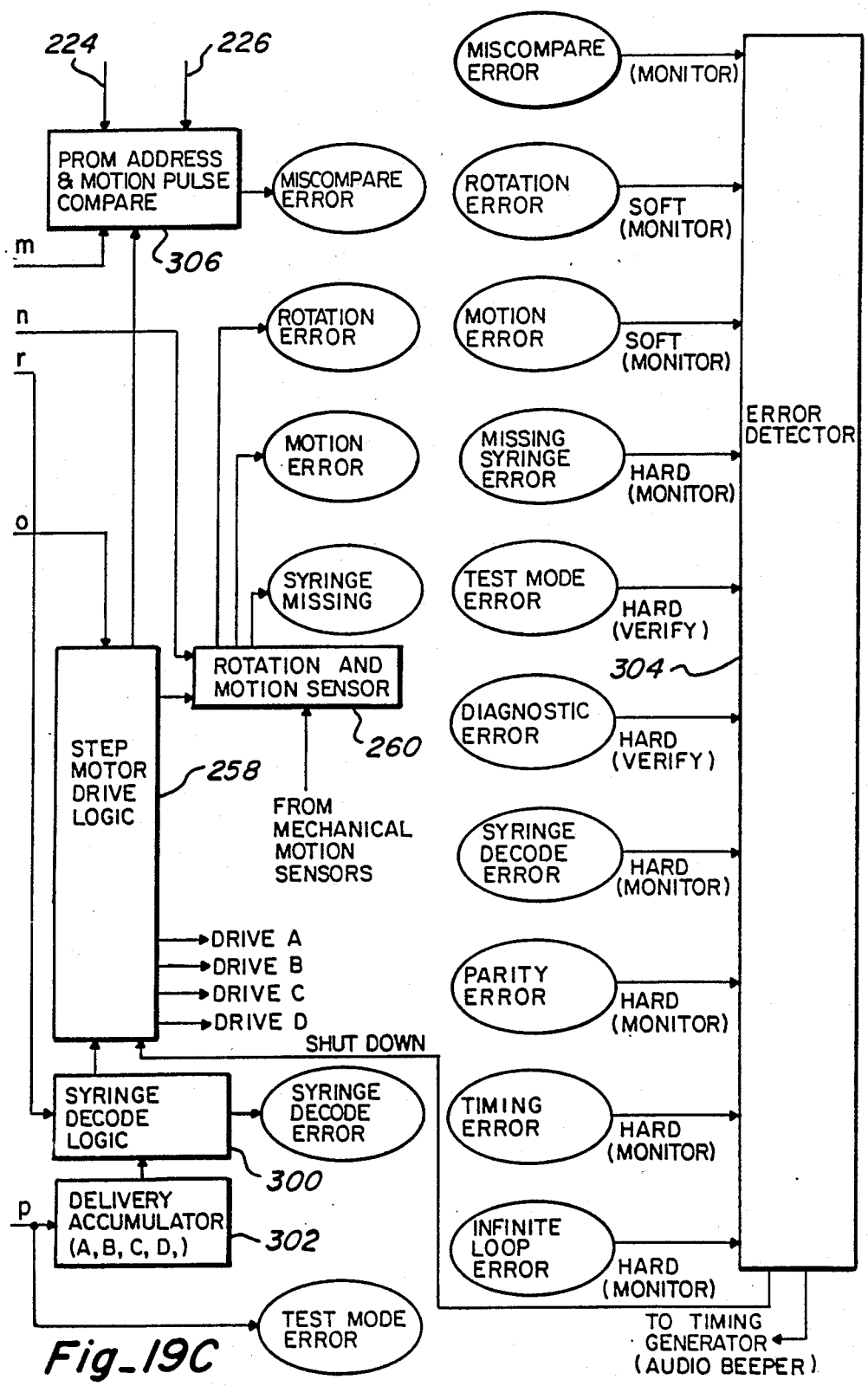

State machine 202 is shown in greater detail in FIGS. 19A, 19B and 19C. State machine 204 is identical to state machine 202. Each is capable of performing error checking and data integrity verification to assure failsafe operation of the electronics. To aid in understanding, the main components of the state machine have been shown in FIGS. 19A, 19B and 19C in rectangular boxes while functions associated with error detection have been shown by ovals.

As shown in FIGS. 19A, 19B and 19C, the major functional areas of the state machine are shiftable memory array 248 and associated circuitry; state logic 250; timing generator 252; PROM data handling circuitry 254 (for PROM cartridge 126); hardware multiplier circuitry 256; motor drive logic 258; and motion feedback sensor unit 260 (including sensors 78 and 154).

Each state machine is a serial design in which data is handled one bit at a time. The device uses shiftable memory array (or shift register memory array 248), consisting of 11 shift registers 264, as indicated in FIG. 19B, each 15 bits wide. As indicated in FIGS. 19A and 19B, each register 264 is connected at the input side to register enable 266 and at the output side to register data select 268. The shift registers thus have a single input and a single output and there is no access to data along the length of the register. Data is continually circulated through each register as it is accessed.

The shift registers are clocked by the 32.768 KHz main clock resulting in a 15 phase clocking cycle of duration $15 \times (1/32.768) = 0.0004577637$ seconds = 458 microseconds, and this is called the basic machine state time. Data is held as 15 bit words within each register. Reading or writing to a register is done one bit at a time and a read or write cycle takes 458 microseconds.

The array is addressed in one of four repeating address patterns as controlled by address sequence control 270 (FIG. 19A), and as directed by the main state logic 250. The particular addressing mode depends on which of the four main operation modes the machine is executing. The relationship between addressing modes and main operation modes is shown in the following table:

| ADDRESSING MODE | MAIN OPERATION MODE |
| --- | --- |
| RESET | Power up & PROM reset only |
| MINUTE/DELIVERY | Delivery mode & Clear Q Mode |
| FETCH MODE | Fetch mode |
| TEST MODE | Test mode |

As indicated, this design utilizes 11 functional registers but the addresses output by the address sequence control cover the range of 0 through 15 (decimal) thus accessing a total of 240 bits, only 165 of which are useful. Registers are numbered by their actual binary addresses, as shown in FIG. 19B. The basic memory cycle is 240 bits long, and the synch signal on the communications port has a period of 240 bits.

The relationship governing fluid delivery from the pump is given by number of motor steps per minute = $Q \times E \times M/32$, where Q is a 5 bit number referred to as "fluid quanta" and is the parameter which is changed each minute for up to 24 hours by the PROM cartridge in order to set delivery for that minute (the high order bit is always zero, allowing an adjustment range of 0-15), E is a 5 bit number referred to as an "envelope" which can be changed each hour for up to 31 days by the PROM cartridge in order to modify by a scale factor the fluid delivery for that minute, and M is a 5 bit number referred to as a "multiplier" (its intended use is to modify delivery by way of the communications port).

There are 11 dedicated registers 264 in shiftable memory array 248. Their numbers correspond to their binary addresses, and their use is as follows:

Register 0 (time of minute) is used as a 15 bit counter whose purpose is to signal the passing of a minute by overflowing to the all zero state, to implement the one bit multiplier algorithm, and to make exact machine time available to the communications port (it is incremented every fourth machine state time, or every 1.83105646 ms no matter what addressing or operation mode the state machine is in);

Registers 2, 6, 10, 14 (QEM A, B, C, D) carry the basic fluid delivery Q, E, and M data for channels A through D, obtained from the PROM cartridge or the communications port looking at the output (right hand side of a register) Q appears first, E second and M third, however, in order to make the hardware multiplier circuitry and algorithm function properly, the MSB must appear first for Q, E, and M as data is clocked out serially;

Register 4 (QEM Diagnostic) contains diagnostic patterns "0" or "1" which are obtained from the PROM cartridge once each minute, and have been placed there by the computer software (this register is read once every eight basic machine states, or 3.66210936 ms, throughout the delivery cycle and compared to the appropriate pattern hardwired in the logic, and thus, in the 58.06 second delivery period, it is read and compared to hardware 15,855 times);

Register 1 (Initialization (INI) Program Counter) contains a 15 bit number, high order bit always zero, which is PROM address, and is referred to as the INI program counter (at reset and at the start of every new minute instructions in the PROM cartridge pointed to by the INI counter are run in order to accomplish state machine "housekeeping" tasks, audio beeper commands and minute-alternating patterns 1 and 0 are set by the initialization code and the INI counter is incremented by the state machine);

Register 5 (Day Program Counter) contains a 15 bit number, high order bit always zero, which is a PROM address, and is referred to as the DAY program counter (the instructions in the PROM cartridge pointed to by the DAY program counter are used to set the envelope (E) number each hour for a total of 744 times or 31 days, thereby modifying the fluid delivery scale factor);

Register 9 (Minute Program Counter) contains a 15 bit number, high order bit always zero, which is a PROM address, and is referred to as the MIN program counter (the instructions in PROM pointed to by the minute program counter execute each minute for a maximum of 1440 minutes, and, instructions run by the minute program counter normally pass the Q number and duty cycle setting information);

Register 13 (Demand Program Counter) contains a 15 bit number, high order bit always zero, which is a PROM address, and is referred to a the DMD program counter (instructions pointed to by this series of addresses execute only if a patient-initiated demand request is made, and any fluid delivery channel can be caused to delivery fluid in any authorized manner under control of the program pointed to by the DMD counter, with a delivery time limitation normally imposed of three hours); and Register 12 (Spare) can be used to store an arbitrary 15 bit number, such as a patient ID.

State logic 250 controls the flow of operations in the state machine and causes the repeating minute sequence of operations shown in FIGS. 19A, 19B and 19C to occur. As indicated, the main interfaces of state logic 250 are front panel 208, address sequence control 270, increment invert pass 272 (connected with communications logic 273 and data multiplexer 274) which is the incrementer for the shift register member array, one bit multiplier 276, instruction decoder 278, and timing generator 252. In addition, state logic 250 is reset by power up reset 280 and receives another input from top of minute detector 282.

Timing generator 252 generates all timing signals required by the logic of the main and error state machines. In particular, it compares the main and reference clocks and declares an error if they differ by more than one part in 15. It generates the audio alarm tones and if one clock fails completely it switches the alarm generator to the remaining clock. Timing generator 252 also generates the 30 microsecond power strobe for reading PROM cartridge 126.

As is also indicated in FIGS. 19A and 19B, PROM cartridge 126 provides an output to PROM instruction buffer 284 and receives inputs from PROM power strobe 206 and PROM address register 286 (which receives an input from PROM address and time of minute buffer 288). PROM instruction buffer 284 supplies outputs to instruction decoder 278 and PROM data serializer 290. Holding register 292 receives inputs from instruction decoder 278 and PROM data serializer 290 and supplies outputs to data multiplexer 274, duty cycle register 294 (which supplies an input to step motor drive logic 258), and to clock pause/stop select 296 (which causes timing generator 252 to read a decoded instruction from the PROM cartridge that tells it whether to advance the profile, or stop the profile, when the pump is stopped either from the front panel or by a PROM instruction). Instruction decoder 278 also supplies an output through QQ latch 298 to state logic 250, to timing generator 252, to rotation and motion sensor 260, and to syringe decode logic 300 (which receives an input from delivery accumulator 302 connected with one bit multiplier 276).

The PROM cartridge is powered on and read for 30 microseconds. Each eight bit data word is placed in buffer 282 and then serialized into a serial bit stream by PROM data serializer 288 for use by the shift register memory array as one bit serial data. Instruction decoder 278 operates on parallel 8 bit data and decodes received instruction.

The above-referenced basic fluid delivery equation requires the multiplication of three binary numbers serially, and conversion of the result to step motor commands. To accomplish this, an algorithm is used which checks bits, one at a time, from the time of minute register (register 0) and also checks bits in the QEM register of the channel for which the multiplication is to be done. The time of minute register and the QEM register of interest are read during the basic machine cycle which occurs during the delivery mode portion of the minute. The algorithm operates as follows:

Start at time of minute bit 0, move left, looking for the first (1) bit;

If a 1 is found before reaching bit 5, continue to next step, but if bit 5 is reached without encountering a 1, exit;

Check corresponding bit in the QEM register (now in the Q section);

If a 1 is found in this bit, go to the next step, otherwise exit algorithm;

Move to bit 5 in the time of minute, search left looking for first 1 bit before reaching bit 10;

If a 1 is found, go to next step, but if bit 10 is reached with no 1 found, exit;

Check corresponding bit in QEM register, now in the E section;

If this bit is also 1, go to the next step, but if not; exit algorithm;

Move to bit 10 in time of minute register, search left looking for first 1 before the end of the register;

If a 1 is found, continue to the next step, but if the end of the register is reached with no 1 found, exit;

Check corresponding bit in the QEM register (now in the M section);

If the matching bit is also 1, continue, but if no match, exit algorithm;

If this point is reached in the algorithm, increment the delivery accumulator; and If the delivery accumulator reaches 32, issue a motor step command for this channel and reset the delivery accumulator.

Note that for this algorithm to function properly, the QEM must be actually loaded with the Q, E, and M bits with MSB first.

The logic which drives the four step motors must perform 8 functions, as follows: Accept a step drive command from the delivery accumulator; route a step command to the correct channel; generate a variable duty cycle switched step waveform for each channel (the following duty cycles are available from computer software by way of the instruction decode function: 88.8%, 87.5%, 85.7%, 83.3%, 80%, 75%, 66.6%, 50%); generate the proper "Left" and "Right" drive signals to drive the bipolar step motor through the Hybrid motor drive circuit; turn off the drive for one clock period (30.5 microseconds) before applying the brake signal; provide 4 motor sync signals to the motion sensor logic; provide 4 motor drive sync signals for comparison with a second gate array; and provide a shutdown function from the error detector.

The motion feedback functional block must perform the following functions: Search for and sync to rotation sensor and plunger (rack) sensor physical edges on startup; after edge sync is accomplished, decrease strobe period to conserve power; check for correct 1/0 pattern from both rotation and plunger feedback signals; and initiate error signals if motion is incorrect.

The optical emitters (LEDs) for both the rotation and rack sensors are always strobed in series. On startup, they are pulsed every 8 motor steps for each channel until the first 0 to 1 (light to dark) transition is sensed for both the rotation and rack sensor for that channel. The sensor is now synchronized to an edge. At this point the strobe count is adjusted until strobing occurs in the center of the optical region for that sensor and the sensors are strobed every 64 motor steps thereafter for motion feedback information.

The centers of the rotation sensor regions are 64 motor steps apart, and the reflective band centers on the plunger sensor are 1024 steps apart.

On startup, the rotation sensor can wait as many as 160 motor steps before detecting a stalled motor. The rack sensor can wait as many as 2560 motor steps before detecting a stalled rack.

During normal operation, the maximum amount of incorrect motion for the rotation sensor before an error is detected is 96 motor steps. The maximum amount of incorrect motion for the rack sensor before an error is detected is 1536 steps.

There are 10 conditions for which errors can be declared by the error detection within the gate array, and they are indicated in FIGS. 19A, 19B and 19C by ovals connected to error detector 304, as follows:

1. Internal Miscompare Error—Hard Error

There is a discrepancy between calculated PROM addresses or motor step commands produced by master or slave gate arrays (developed by comparison of the master and slave gate arrays at PROM address and motion pulse compare 306);

2. Rotation Error—Soft Error

The angular motion of the perforated sense wheel, located on the second state of the gear drive, is incorrect (developed by rotation and motion sensor 260);

3. Rack or Plunger (Motion) Error—Soft Error

The linear motion of the syringe plunger is incorrect (developed by rotation and motion sensor 260);

4. Missing Syringe Error—Hard Error

A syringe in a particular channel is missing although the computer program requires a syringe in that channel. This is detected as a rotation error (developed by rotation and motion sensor 260). For this test the step motor duty cycle is set intentionally low by software so that there should be a rotation error in any channel containing a syringe, due to the mechanical drag of that syringe. Channels having missing syringes should not experience a motion error. For this test the pump is "rescued" from a normal soft error by appropriate logic, and any channel not experiencing the symptoms of a rotation soft error, when such symptoms should be experiences, is considered to have a missing syringe, and a hard error is issued;

5. Test Mode Error—Hard Error

Valid QEM delivery data is inverted, saved in a buffer, inverted a second time, and written back to its register in the shift register memory array. The two words are compared and should not have any bits in common. The two words are then sent to one bit multiplier 276 one word masquerading as the top of minute data which is normally used in this operation. The one bit multiplier should not produce an output. If either of these conditions fails, a hard error is issued;

6. Diagnostic Error—Hard Error

The "Pattern 1, Pattern 0" alternate minute comparison (provided in test pattern 1 or 0 unit 308) is done from the QEM diagnostic register throughout the duration of the delivery mode. If the comparison fails, a hard error is issued;

7. Syringe Decode Error—Hard Error

If two channels are commanded to output a motor step simultaneously, a hard error is issued (developed at syringe decode logic 300);

8. Parity Error—Hard Error

Each time the PROM cartridge is read during the fetch mode, logic checks for odd parity. If parity is incorrect, a hard error is issued (detected at instruction decoder 278);

9. Timing Error—Hard Error

If the main and reference clocks differ by 1 part in 15, a hard error is issued. If either clock fails entirely, a hard error is issued and the audio alarm uses the remaining clock to signal the alarm (detected at timing generator 252); and 10. Infinite Loop Error—Hard Error The fetch mode allows a maximum of one minute of "reads" of the PROM cartridge. If the software program terminates improperly causing the fetch mode to extend to the next top of minute, a hard error is issued. Delivery is inhibited while the state machine is still in fetch mode (detected at state logic 250).

Timing conventions are adhered to in the operation of the state machine as it executes each of its four modes. The clock frequency is 32.768 KHz, and the clock period (P) is 1/32.768=30.517578 microseconds. The state machine operates on a 15 phase clock. Each phase is one clock period long. The basic machine state time is 15 clock periods, and corresponds to the time taken to read or write a shift register.

State time=15P=457.76367 microseconds

The time of minute (TOM) register is a 15 bit binary counter and is incremented every four machine states.

TOM=4 states
TOM=1.8310546 milliseconds

The time minute register goes through a complete count cycle in 32,768×1.8310546 mS=60 seconds.

Every addressing sequence into shift memory array 248 is at least 8 states long and is called a machine cycle. When some of the addresses are unused a "NO-OP" is indicated. Addresses are not skipped. NO OP is a register fetch in which nothing is done with the data obtained.

Machine Cycle=8 states=3.66210936 mS

Figure 20:
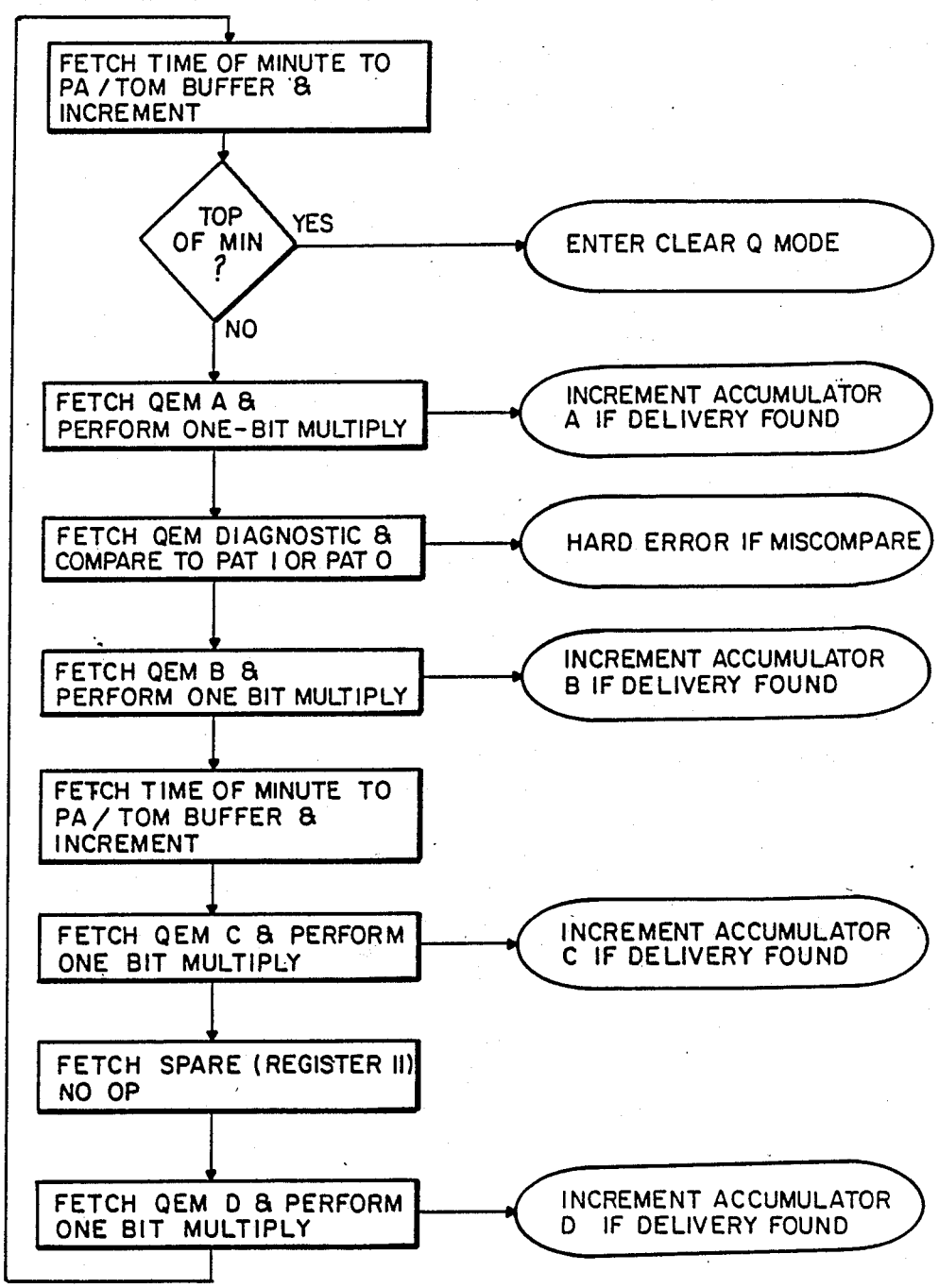
FIGS. 20 through 22 are functional flow diagrams for effecting specified modes of operation of the apparatus shown in FIGS. 17 through 19.
Figure 21:
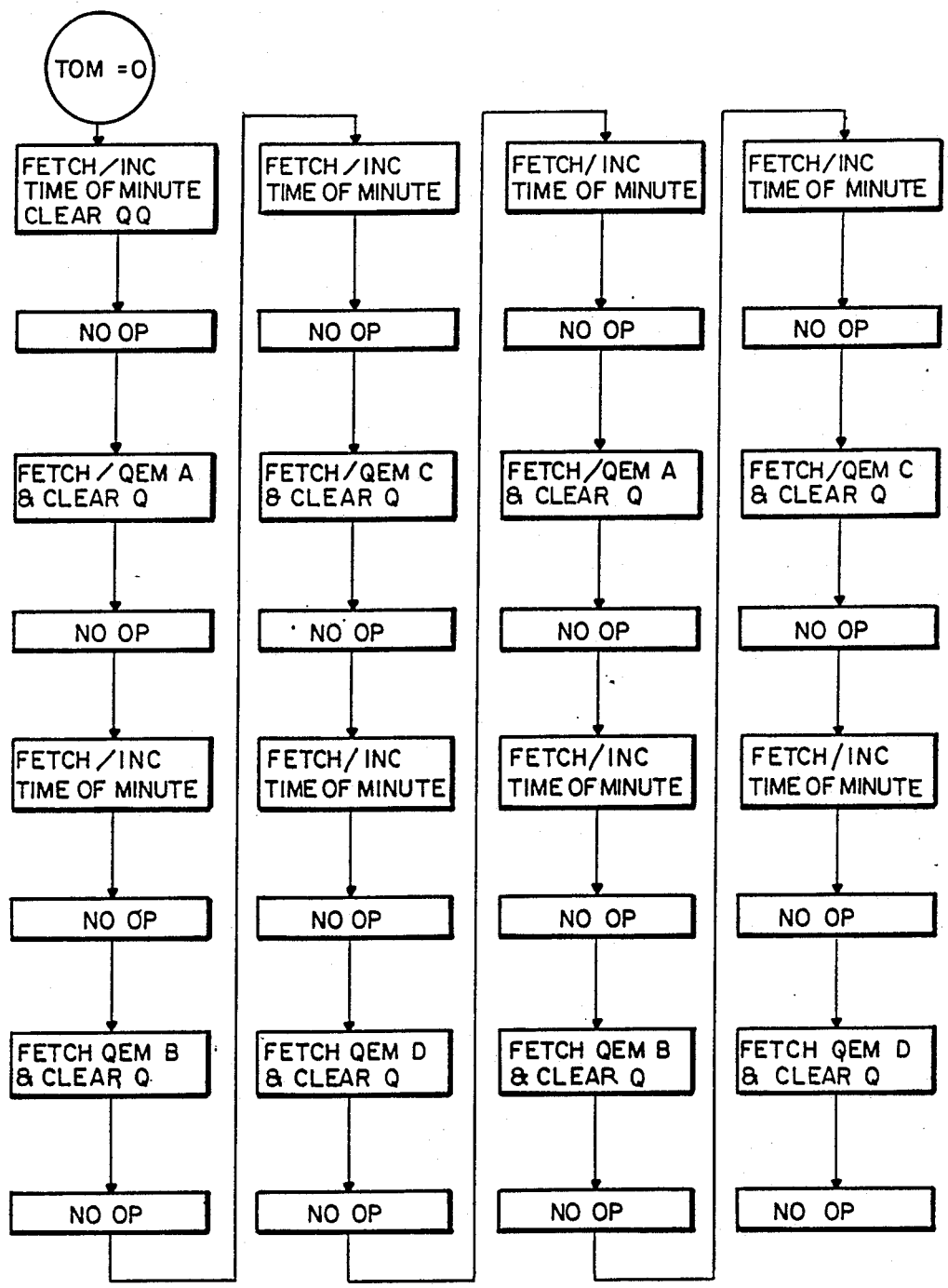
Figure 22:
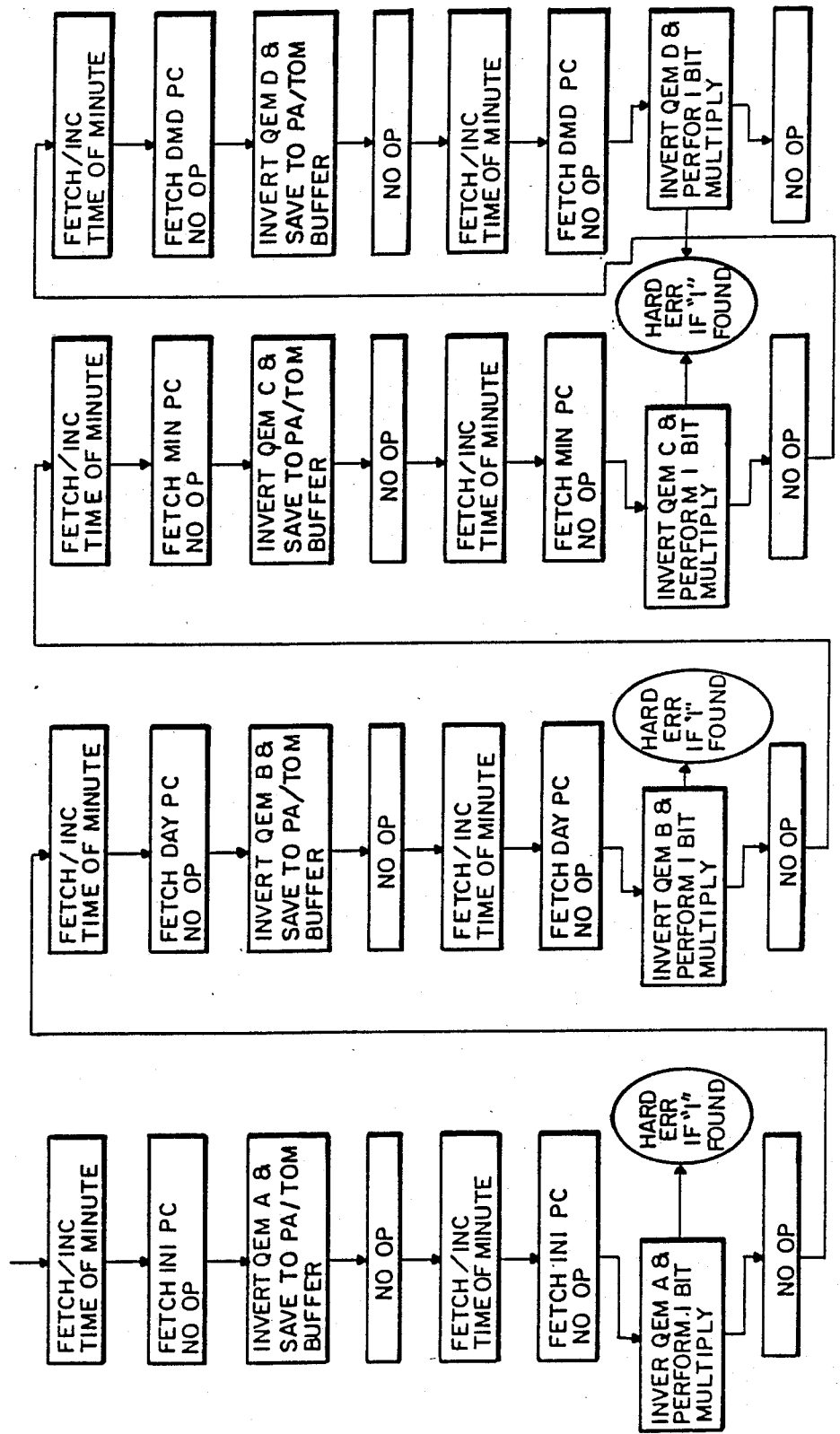

This leads to a total of 16,384 machine cycles in a minute of operation. The bit clock (main clock) is synchronous with all timing events in each of the four modes in the machine. The breakdown of the modes by machine cycles is as follows:

Clear Q Mode: 4 Cycles
Fetch Mode: 2-521 Cycles
Test Mode: 4 Cycles
Delivery Mode: 15,855-16,374 Cycles
Total: 16,384 cycles or 1,966,080 bits FIG. 20 sets forth the delivery mode diagram for the state machine, FIG. 21 sets forth the clear Q mode diagram for the state machine, and FIG. 22 gives the test mode diagram for the state machine.

The delivery unit, or pump, 200 described herein has been commercially configured as a device, or product, that is lightweight (about 3.5 pounds) and of sufficiently small dimensions (about 2¾ inches×5½ inches×9 inches) so as to make the product readily transportable and wearable, provides ease of use even with complex flow profiles, has relatively long battery life (about two weeks or more of continuous operation) and provides overall system safety.

As can be appreciated from the foregoing, this invention provides a substantially failsafe device and method for controlling delivery of fluid from syringes.

What is claimed is:

1. A compact device for controlling delivery of fluid from a syringe having a piston the movement of which in a predetermined direction causes said fluid to be expelled from said syringe, said device comprising:
  a stepper motor having a rotatable motor shaft;
  pulse generating means including first and second state machines operating in parallel with respect to one another and connected in common with said stepper motor to provide pulses thereto, when said first and second state machines provide like outputs, for causing rotation of said motor shaft by increments, said first and second state machines including error monitoring means for monitoring said device to determine error in delivery of fluid from said syringe and precluding application of pulses to said stepper motor when said error is determined by said error monitoring means to thereby enhance safe delivery of fluid from said syringe; and
  motion translation means connected with said motor shaft and adapted to be connected with said piston for causing movement of said piston in said predetermined direction in response to said incremental rotation of said motor shaft.

2. The device of claim 1 wherein said device includes battery means for providing the sole power for powering said device.

3. The device of claim 1 wherein said motion translation means includes a rack for connection with said piston and a pinion driven by said motor shaft through a gearing arrangement.

4. The device of claim 3 wherein said rack is formed by a plurality of hinged segments.

5. The device of claim 1 wherein said motion translation means includes a one-way ball drive engagable with said motor shaft to permit rotation of said motor shaft in only one predetermined direction.

6. The device of claim 1 wherein said pulse generating means includes a pair of clocking means each of which is connected with said first and second state machines to further reduce error by requiring predetermined agreement between each of said clocking means.

7. A compact device for controlling delivery of fluid from a syringe having a piston the movement of which in a predetermined direction causes said fluid to be expelled from said syringe, said device comprising:
  a stepper motor having a rotatable motor shaft;
  pulse generating means connected with said stepper motor to provide pulses thereto for causing rotation of said motor shaft by increments, said pulse generating means including means providing data for enabling pulse creation and error monitoring means for determining error in delivery of fluid from said syringe and precluding application of pulses to said stepper motor when said error is determined by said error monitoring means to thereby enhance safe delivery of fluid from said syringe, said error monitoring means including verifying means for verifying the integrity of said data utilized in causing said pulse generating means to create said pulses; and
  motion translation means connected with said motor shaft and adapted to be connected with said piston for causing movement of said piston in said predetermined direction in response to said incremental rotation of said motor shaft.

8. A compact device for controlling delivery of fluid from a syringe having a piston the movement of which in a predetermined direction causes said fluid to be expelled from said syringe, said device comprising:
  a stepper motor having a rotatable motor shaft;
  pulse generating means connected with said stepper motor to provide pulses thereto for causing rotation of said motor shaft by increments;
  braking means connected with said stepper motor to cause termination of rotation of said motor shaft upon termination of each of said pulses applied to said motor shaft by said pulse generating means; and
  motion translation means connected with said motor shaft and said piston for causing movement of said piston in said predetermined direction in response to said incremental rotation of said motor shaft, said motion translation means including a gearing arrangement having apertures therein, a rack adapted to be connected with said piston and having distinguishable stripes thereon, and a pinion connected with said stepper motor through said gearing arrangement;

a first sensor responsive to said distinguishable stripes on said rack; and a second sensor responsive to movement of said apertures in said gearing arrangement to thereby determine that fluid has been discharged from said syringe.

9. The device of claim 8 wherein said device includes power supply means adapted to receive a pair of batteries, said batteries providing the sole power for operation of said device, and said power supply means being configured so that either of said batteries can power the device in the absence of power supplied from the other.

10. The device of claim 8 wherein said pulse generating means includes error monitoring means for determining error in delivery of fluid from said syringe and precluding application of pulses to said stepper motor when said error is determined by said error monitoring means to thereby enhance safe delivery of fluids from said syringe.

11. In a device for effecting delivery of fluid through movement of a discharge causing element, a control system for controlling movement of said discharge causing element, said control system comprising:

profile carrying means for providing a predetermined profile of fluid to be delivered, said profile carrying means including a removable logic cartridge;

drive means connected with said profile carrying means for providing an output for causing movement of said discharge causing element according to said profile, said drive means including first and second substantially identical state machines connected with said removable logic cartridge and in parallel with respect to one another and providing independent outputs, said first and second state machines including error determining means to determine error in said drive means by comparison of said independent outputs, said error determining means also being responsive to said profile carrying means for determining error in said profile as well as in said drive means and providing an error indication in response thereto; and means for receiving said error indications and responsive thereto providing at least one of an error indication and termination of fluid delivery.

12. The system of claim 11 wherein said system includes first and second clocking means which operate at the same frequency and each of which is connected with different ones of said first and second state machines.

13. The system of claim 11 wherein said state machines also provide a plurality of data integrity verifications.

14. A method for monitoring safe delivery of fluid from a syringe having a piston the movement of which is effected by electronic signals supplied to a piston actuating element, said method comprising:

providing a profile of fluid flow to be delivered from said syringe;

providing first and second substantially identical state machines for generating said electronic signals responsive to said profile of fluid and coupling said electronic signals to said piston actuating element;

monitoring operation of said state machines and said profile of fluid to be delivered by providing separate outputs from each of state machines and comparing said outputs to enhance safe operation of said state machines by detecting errors therein; and utilizing detected errors to effect safe operation of said state machines by at least one of indicating said detected errors and terminating delivery of fluid from said syringe.

15. The method of claim 14 wherein said method includes monitoring said state machines at least every sixty seconds to determine if error exists therein.

16. A method for monitoring safe delivery of fluid from a syringe having a piston the movement of which is effected by electronic signals supplied to a piston actuating element, said method comprising:

providing a profile in one minute increments of fluid flow to be delivered from said syringe;

providing a state machine for successively obtaining each one minute increment of fluid flow profile and generating therefrom said electronic signals responsive to said increment of fluid flow profile then obtained and coupling said electronic signals to said piston actuating element;

monitoring operation of said state machine and said profile of fluid then to be delivered to detect errors therein; and utilizing detected errors to effect safe operation of said state machine by at least one of indicating said detected errors and terminating delivery of fluid from said syringe.

17. The method of claim 16 wherein said method includes preparing said fluid flow profile for a time period of up to 31 days for effecting delivery of fluid from said syringe.

18. A device for monitoring safe delivery of fluid from a syringe having a piston the movement of which in a direction to expel fluid from said syringe is effected by electronic signals supplied to a piston actuating element, said device comprising:

control means providing a profile of fluid flow to be delivered from said syringe;

signal generating means having first and second substantially identical state machines connected with said control means for generating said electronic signals responsive to said profile of fluid from said control means and coupling said electronic signals to said piston actuating element, said first and second state machines including monitoring means for monitoring operation of said state machines and said profile of fluid to be delivered by comparing separate outputs from each of said state machines to enhance safe operation of said state machines by detecting errors therein; and utilization means connected with said monitoring means and utilizing detected errors received therefrom to effect safe operation of said state machines by at least one of indicating said detected errors and terminating delivery of fluid from said syringe.

* * * * *